(12) United States Patent
Schunk et al.

(10) Patent No.: US 7,960,404 B2
(45) Date of Patent: Jun. 14, 2011

(54) SPIROCYCLIC CYCLOHEXANE COMPOUNDS

(75) Inventors: Stefan Schunk, Aachen (DE); Derek Saunders, Aachen (DE); Stephanie Harlfinger, Cologne (DE); Sonja Steufmehl, Linnich (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/545,261

(22) Filed: Aug. 21, 2009

(65) Prior Publication Data

US 2010/0048553 A1   Feb. 25, 2010

Related U.S. Application Data

(63) Continuation of application No. PCT/EP2008/001271, filed on Feb. 19, 2008.

(30) Foreign Application Priority Data

Feb. 22, 2007   (DE) .................. 10 2007 009 319

(51) Int. Cl.
| | |
|---|---|
| A61K 31/437 | (2006.01) |
| A61K 31/404 | (2006.01) |
| C07D 401/04 | (2006.01) |
| C07D 401/14 | (2006.01) |
| C07D 209/56 | (2006.01) |

(52) U.S. Cl. ............ 514/278; 514/409; 546/18; 548/407
(58) Field of Classification Search ............... 514/232.8, 514/254.08, 278; 544/70, 230; 546/18
See application file for complete search history.

(56) References Cited

U.S. PATENT DOCUMENTS

| | | | |
|---|---|---|---|
| 7,332,519 B2 | 2/2008 | Hinze et al. | |
| 7,547,707 B2 | 6/2009 | Hinze et al. | |
| 2005/0192333 A1 | 9/2005 | Hinze et al. | |
| 2008/0125475 A1 | 5/2008 | Linz et al. | |
| 2008/0221141 A1 | 9/2008 | Friderichs et al. | |
| 2009/0163716 A1 | 6/2009 | Hinze et al. | |

FOREIGN PATENT DOCUMENTS

| | | |
|---|---|---|
| DE | 102 52 667 A1 | 5/2004 |
| DE | 103 60 792 A1 | 7/2005 |
| DE | 10 2005 016 460 A1 | 10/2006 |
| WO | WO 2004/043967 A1 | 6/2004 |
| WO | WO 2005/066183 A1 | 7/2005 |
| WO | WO 2006/108565 A1 | 10/2006 |

OTHER PUBLICATIONS

Fuad A. Abdulla et al., "Axotomy Reduces the Effect of Analgesic Opioids Yet Increases the Effect of Nociceptin on Dorsal Root Ganglion Neurons", The Journal of Neuroscience, Dec. 1, 1998, 18(23): 9685-9694.

Anthony L. Beck et al., "Synthesis of 3,4-Bridged Indoles by Photocyclisation Reactions. Part 2.[1] Photocyclisation of Halogenoacetyl Tryptophol Derivatives and α-Chloro Indol-3-ylalkanoate Esters", J. Chem. Soc. Perkin Trans. 1, pp. 813-821, 1992.

Girolamo Calo et al., "Pharmacology of nociceptin and its receptor: a novel therapeutic target", British Journal of Pharmacology (2000) 129, 1261-1283, Macmillan Publishers Ltd.

Simon J. Garden et al., "A versatile synthetic methodology for the synthesis of tryptophols", Tetrahedron 58 (2002) 8399-8412, Pergamon.

Francois Jenck et al., "Orphanin FQ acts as an anxiolytic to attenuate behavioral responses to stress", Proc. Natl. Acad. Sci. USA, vol. 94, pp. 14854-14858, Dec. 1997, Neurobiology.

I. Jirkovsky et al., "Synthesis of 1,3,4,9-Tetrahydro-1-alkylthiopyrano [3,4-b] indole-1-acetic Acids. The Sulfur Isoster of Prodolic Acid", vol. 12, pp. 937-940, Ayerst Research Laboratories, Montreal, Quebec, Canada, Oct. 1975.

Michael A. King et al., "Spinal analgesic activity of orphanin FQ/nociceptin and its fragments", Neuroscience Letters 223 (1997) 113-116, Elsevier Science Letters.

Daniel Lednicer et al., "4-Amino-4-arylcyclohexanones and Their Derivatives, a Novel Class of Analgesics. 1. Modification of the Aryl Ring", The Upjohn Company, Research Laboratories, Kalamazoo, Michigan.

Toshiya Manabe et al., "Facilitation of long-term potentiation and memory in mice lacking nociceptin receptors", Letters to Nature, vol. 394, pp. 577- 581, Aug. 6, 1998, Macmillan Publishers Ltd.

Jean-Claude Meunier et al., "Isolation and structure of the endogenous agonist of opioid receptor-like ORL₁ receptor" Letters of Nature, vol. 377, pp. 532-535, Oct. 12, 1995.

J. S. Mogil et al., "Orphanin FQ is a Functional Anti-Opioid Peptide", Letter to Neuroscience, Neuroscience vol. 75, No. 2, pp. 333-337, 1996, Elsevier Science Ltd., Pergamon, Great Britain.

Miyuki Nishi et al., "Unrestrained nociceptive response and disregulation of hearing ability in mice lacking the nociceptin/orphaninFQ receptor", The EMBO Journal, vol. 16, No. 8, pp. 1858-1864, 1997, Oxford University Press.

Rainer K. Reinscheid et al., "Orphanin FQ: A Neuropeptide That Activates an Opioidlike G Protein-Coupled Receptor", Science, vol. 270, pp. 792-794, Nov. 3, 1995.

(Continued)

*Primary Examiner* — Kamal Saeed
*Assistant Examiner* — Kristin Bianchi
(74) *Attorney, Agent, or Firm* — Crowell & Moring LLP

(57) ABSTRACT

Spirocyclic cyclohexane compounds corresponding to formula I

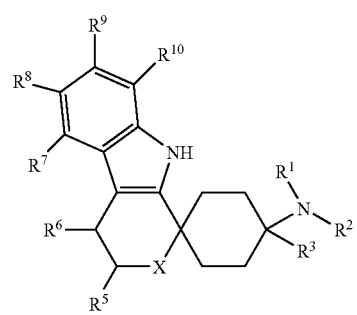

in which $R^1$ and $R^2$ form a pyrrolidine ring or an azetidine ring and which exhibit increased metabolic stability, a process for producing such spirocyclic cyclohexane compounds, pharmaceutical compositions containing such spirocyclic cyclohexane compounds, and the use of such spirocyclic cyclohexane compounds to treat or inhibit pain and/or other disorders.

23 Claims, No Drawings

OTHER PUBLICATIONS

Van Bac et al., "New Strategy in the Stereocontrolled Synthesis of the Spiro Ketal Subunit of Milbemycins", Tetrahedron Letters, vol. 29, No. 23, pp. 2819-2822, 1988, Pergamon Press plc, Great Britain.

Marco Bandini et al., "$InBr_3$-Catalyzed Friedel-Crafts Addition of Indoles to Chiral Aromatic Epoxides: A Facile Route to Enantiopure Indolyl Derivatives", JOC Note, J. Org. Chem. 2002, 67, 5386-5389.

Peter D. Davis et al., "Inhibitors of Protein Kinase C. 1.[1] 2,3-Bisarylmaleimides", J. Med. Chem. 1992, 35, 177-184.

D. Mark Gleave et al., "Synthesis and Antibacterial Activity of [6,5,5] and [6,6,5] Tricyclic Fused Oxazolidinones", Bioorganic & Medicinal Chemistry Letters 8 (1998) 1231-1236.

Katsuya Kato et al., "Synthesis of α-trifluoromethylated indoleacetic acid: a potential peroxidase-stable plant growth regulator", Journal of Fluorine Chemistry 99 (1999) 5-7.

Alan R. Katritzky et al., "The Chemistry of N-Substituted Benzotriazoles; Part 11. 1 The Preparation of Tertiary Amines Containing Tertiary-Alkyl Groups from Ketones, Secondary Amines, and Organometallic Reagants", Communications, Synthesis, pp. 66-69, Jan. 1989.

Alan H. Katz et al., "Synthesis and Analgesic Activity of Pemedolac (cis-1-Ethyl-1,3,4,9-tetrahydro-4-(phenylmethyl) pyrano[3,4-b]indole-1-acetic Acid)", J. Med. Chem. 1988, 31, 1244-1250.

Chunrong Ma et al., "Efficient Asymmetric Synthesis of Biologically Important Tryptophan Analogues via a Palladium-Mediated Heteroannulation Reaction", J. Org. Chem. 2001, 66, 4525-4542.

T. Sandmeyer, "Ueber Isonitrosoacetanilide and deren Kondensation zu Isatinen", The British Library, pp. 234-242, 1919.

Masafumi Yamagishi et al., "Biological Activities and Quantitative Structure-Activity Relationships of Spiro[imidazolidine-4,4'(V'H)-quinazoline]-2,2',5(3'H)-triones as Aldose Reductase Inhibitors", J. Med. Chem. 1992, 35, 2085-2094.

Tetsuro Shinada et al., "Facile Synthesis of 6-Hydroxyindole-3-acetic Acid: On the Structure of the Aromatic Subunit of Nephilatoxin-1~6", Tetrahedron Letters, vol. 37, No. 39, pp. 7099-7102, 1996, Great Britain.

Aeri Park et al., "New solid-state chemistry technologies to bring better drugs to market: knowledge-based decision making", Expert Opin. Drug Discov. (2007) 2(1), pp. 145-154.

Ali Ardati et al., "Interaction of [$^3$H] Orphanin FQ and $^{125}$I-Tyr14-Orphanin FQ with the Orphanin FQ Receptor: Kinetics and Modulation by Cations and Guanine Nucleotides", Molecular Pharmacology, vol. 51, pp. 816-824 (1997).

German Search Report dated Aug. 28, 2007 w/partial English translation (nine (9) pages).

International Search Report dated Jul. 15, 2008 w/partial English translation (four (4) pages).

SPIROCYCLIC CYCLOHEXANE COMPOUNDS

CROSS REFERENCE TO RELATED APPLICATIONS

This application is a continuation of international patent application no. PCT/EP2008/001271, filed Feb. 19, 2008 designating the United States of America and published in German on Aug. 28, 2008 as WO 2008/101660, the entire disclosure of which is incorporated herein by reference. Priority is claimed based on Federal Republic of Germany patent application no. DE 10 2007 009 319.7, filed Feb. 22, 2007.

BACKGROUND OF THE INVENTION

The present invention relates to spirocyclic cyclohexane derivatives, processes for the preparation thereof, pharmaceutical compositions containing these compounds and the use of spirocyclic cyclohexane derivatives for the preparation of pharmaceutical compositions.

The heptadecapeptide nociceptin is an endogenous ligand of the ORL1 (opioid receptor-like) receptor (Meunier et al., Nature 377, 1995, p. 532-535), which belongs to the family of opioid receptors, is to be found in many regions of the brain and spinal cord, and has a high affinity for the ORL1 receptor. The ORL1 receptor is homologous to the μ, κ and δ opioid receptors and the amino acid sequence of the nociceptin peptide displays a strong similarity to those of the known opioid peptides. The activation of the receptor induced by nociceptin leads via the coupling with $G_{i/o}$ proteins to an inhibition of the adenylate cyclase (Meunier et al., Nature 377, 1995, p. 532-535).

After intercerebroventicular application, the nociceptin peptide exhibits pronociceptive and hyperalgesic activity in various animal models (Reinscheid et al., Science 270, 1995, p. 792-794). These findings can be explained as an inhibition of stress-induced analgesia (Mogil et al., Neuroscience 75, 1996, p. 333-337). Anxiolytic activity of the nociceptin could also be demonstrated in this connection (Jenck et al., Proc. Natl. Acad. Sci. USA 94, 1997, 14854-14858).

On the other hand, an antinociceptive effect of nociceptin could also be demonstrated in various animal models, in particular after intrathaecal application. Nociceptin has an antinociceptive effect in various pain models, for example in the tail flick test in mice (King et al., Neurosci. Lett., 223, 1997, 113-116). In models of neuropathic pain, an antinociceptive effect of nociceptin could likewise be detected and was particularly beneficial since the effectiveness of nociceptin increases after axotomy of spinal nerves. This contrasts with conventional opioids, the effectiveness of which decreases under these conditions (Abdulla and Smith, J. Neurosci., 18, 1998, p. 9685-9694).

The ORL1 receptor is also involved in the regulation of further physiological and pathophysiological processes. These include inter alia learning and memory (Manabe et al., Nature, 394, 1997, p. 577-581), hearing capacity (Nishi et al., EMBO J., 16, 1997, p. 1858-1864) and numerous further processes. A synopsis by Calo et al. (Br. J. Pharmacol., 129, 2000, 1261-1283) gives an overview of the indications or biological processes in which the ORL1 receptor plays a part or could very probably play a part. Mentioned inter alia are: analgesics, stimulation and regulation of food intake, effect on μ-agonists such as morphine, treatment of withdrawal symptoms, reduction of the addiction potential of opioids, anxiolysis, modulation of motor activity, memory disorders, epilepsy; modulation of neurotransmitter release, in particular of glutamate, serotonin and dopamine, and hence neurodegenerative diseases; influence on the cardiovascular system, triggering of an erection, diuresis, antinatriuresis, electrolyte balance, arterial blood pressure, water retention disorders, intestinal motility (diarrhoea), relaxation of the respiratory tract, micturation reflex (urinary incontinence). The use of agonists and antagonists as anorectics, analgesics (also when coadministered with opioids) or nootropics is also discussed.

The possible uses of compounds that bind to the ORL1 receptor and activate or inhibit it are correspondingly diverse. In addition, however, opioid receptors such as the μ-receptor, but also the other subtypes of these opioid receptors, namely δ and κ, play an important part in the field of pain therapy and also other of the aforementioned indications. It is accordingly beneficial if the compound also has an effect on these opioid receptors.

WO 2004043967 discloses spirocyclic cyclohexane derivatives having a high affinity for the ORL1 receptor but also for the μ-opioid receptor. WO 2004043967 discloses generic compounds wherein $R^1$ and $R^2$ form a ring, but no example compounds having this structural element are disclosed. Only example compounds in which $R^1$ and $R^2$ denote H or $CH_3$ are disclosed, wherein at least one of the radicals $R^1$ and $R^2$ denotes H. These compounds have an exceptionally high affinity for the μ-opioid or ORL1 receptor, as demonstrated by corresponding data.

Metabolic stability is a critical property for the effectiveness of a compound and hence also for the successful development of a pharmaceutical composition. The compounds disclosed as example compounds in WO 2004043967 are broken down in the organism inter alia by N-demethylation. These metabolites are for their part biologically active again.

Active metabolites have to be thoroughly investigated during the development of pharmaceutical compositions. For that reason it is advantageous to develop compounds which form few metabolites.

SUMMARY OF THE INVENTION

The object of the present invention was to provide pharmaceutical compositions which act to a great extent on the nociceptin/ORL1 receptor system and which have a greater metabolic stability than the compounds disclosed in WO 2004/043967.

Surprisingly it has now been found that certain compounds which although described in generic terms in WO 2004/043967 were not specifically disclosed have a greater metabolic stability than the disclosed example compounds.

The invention therefore provides spirocyclic cyclohexane derivatives having the general formula I

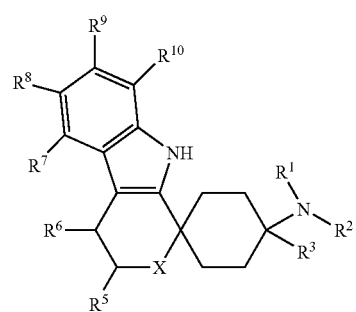

wherein $R^1$ and $R^2$ together form a ring and denote —$CH_2CH_2CH_2$— or —$CH_2CH_2CH_2CH_2$—, or $R^1$ and $R^2$ each denote H;

$R^3$ denotes $C_{1-5}$ alkyl, in each case saturated or unsaturated, branched or unbranched, mono- or polysubstituted or unsubstituted; $C_{3-8}$ cycloalkyl, in each case saturated or unsaturated, mono- or polysubstituted or unsubstituted; aryl or heteroaryl, in each case unsubstituted or mono- or polysubstituted; aryl or $C_{3-8}$ cycloalkyl bonded via a $C_{1-3}$ alkyl group, in each case unsubstituted or mono- or polysubstituted;

$R^5$ denotes =O; H; $C_{1-5}$ alkyl, saturated or unsaturated, branched or unbranched, unsubstituted or mono- or polysubstituted; $COOR^{13}$, $CONR^{13}$, $OR^{13}$; $C_{3-8}$ cycloalkyl, saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted;

$R^6$ denotes H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$ alkyl, saturated or unsaturated, branched or unbranched, unsubstituted or mono- or polysubstituted; $C_{3-8}$ cycloalkyl, saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl unsubstituted or mono- or polysubstituted; or $R^5$ and $R^6$ together denote $(CH_2)_n$ where n=2, 3, 4, 5 or 6, wherein individual hydrogen atoms can also be replaced by F, Cl, Br, I, $NO_2$, $CF_3$, $OR^{13}$, CN or $C_{1-5}$ alkyl;

$R^7$, $R^8$, $R^9$ and $R^{10}$ each independently denote H, F, Cl, Br, I, $NO_2$, $CF_3$, $OR^{13}$, $SR^{13}$, $SO_2R^{13}$, NHC(=O)$NR^{14}R^{15}$, $SO_2NR^{14}R^{15}$, $SO_2OR^{13}$CN, $COOR^{13}$, $NR^{14}R^{15}$; $C_{1-5}$ alkyl, $C_{3-8}$ cycloalkyl, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted; wherein $R^{13}$ denotes H; $C_{1-5}$ alkyl, in each case saturated or unsaturated, branched or unbranched, unsubstituted or mono- or polysubstituted; $C_{3-8}$ cycloalkyl, in each case saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted;

$R^{14}$ and $R^{15}$ each independently denote H; $C_{1-5}$ alkyl, in each case saturated or unsaturated, branched or unbranched, unsubstituted or mono- or polysubstituted; or $C_{3-8}$ cycloalkyl, in each case saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted; or $R^{14}$ and $R^{15}$ together form $CH_2CH_2OCH_2CH_2$, $CH_2CH_2NR^{16}CH_2CH_2$ or $(CH_2)_{3-6}$;

$R^{16}$ denotes H; $C_{1-5}$ alkyl, saturated or unsaturated, branched or unbranched, unsubstituted or mono- or polysubstituted;

X denotes O, S, SO, $SO_2$ or $NR^{17}$;

$R^{17}$ denotes H; $C_{1-5}$ alkyl, saturated or unsaturated, branched or unbranched; $COR^{12}$ or $SO_2R^{12}$, $R^{12}$ denotes H; $C_{1-5}$ alkyl, in each case saturated or unsaturated, branched or unbranched, mono- or polysubstituted or unsubstituted; $C_{3-8}$ cycloalkyl, in each case saturated or unsaturated, mono- or polysubstituted or unsubstituted; aryl or heteroaryl, in each case mono- or polysubstituted or unsubstituted; or aryl, $C_{3-8}$ cycloalkyl or heteroaryl bonded via $C_{1-3}$ alkyl, in each case mono- or polysubstituted or unsubstituted; $OR^{13}$, $NR^{14}R^{15}$;

in the form of the racemate; the enantiomers, diastereomers, mixtures of enantiomers or diastereomers or a single enantiomer or diastereomer; the bases and/or salts of physiologically compatible acids or cations.

If different radicals, for example $R^7$, $R^8$, $R^9$ and $R^{10}$, are combined together or radicals are combined with their substituents, such as for example $OR^{13}$, $SR^{13}$, $SO_2R^{13}$ or $COOR^{13}$, a substituent, for example $R^{13}$, can assume different meanings for two or more radicals, for example $R^7$, $R^8$, $R^9$ and $R^{10}$, within a substance.

The compounds according to the invention bind well to the ORL1 receptor and the μ-opioid receptor.

As used herein the expressions "$C_{1-8}$ alkyl", "$C_{1-5}$ alkyl" and "$C_{1-3}$ alkyl" encompass acyclic saturated or unsaturated hydrocarbon radicals, which can be branched or straight-chained and unsubstituted or mono- or polysubstituted, having 1, 2, 3, 4, 5, 6, 7 or 8 C atoms or 1, 2, 3, 4 or 5 C atoms or 1, 2 or 3 C atoms, i.e. $C_{1-8}$ alkanyls, $C_{2-8}$ alkenyls and $C_{2-8}$ alkynyls or $C_{1-5}$ alkanyls, $C_{2-5}$ alkenyls and $C_{2-5}$ alkynyls or $C_{1-3}$ alkanyls, $C_{2-3}$ alkenyls and $C_{2-3}$ alkynyls. Alkenyls have at least one C=C double bond and alkynyls have at least one C=C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, n-hexyl, 2-hexyl; ethylenyl(vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), 1,1-dimethylethyl, 1,1-dimethylpropyl, butenyl, butynyl, pentenyl, pentynyl, hexyl, hexenyl, hexynyl, heptyl, heptenyl, heptynyl, octyl, octenyl or octynyl. Methyl, ethyl, n-propyl and n-butyl are particularly preferred within the meaning of this invention.

For the purposes of this invention the expression "cycloalkyl" or "$C_{3-8}$ cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or polysubstituted. $C_{3-8}$ cycloalkyl is advantageously selected from the group including cyclopropyl, cyclobutyl, cyclopentyl, cyclohexyl, cycloheptyl, cyclooctyl, cyclopentenyl, cyclohexenyl, cycloheptenyl and cyclooctenyl. Cyclobutyl, cyclopentyl and cyclohexyl are particularly preferred within the meaning of this invention.

The term $(CH_2)_{3-6}$ is understood to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—.

As used herein the expression "aryl" denotes carbocyclic ring systems having up to 14 ring members with at least one aromatic ring, but without heteroatoms in only one of the rings, inter alia phenyls, naphthyls and phenanthrenyls, fluoranthenyls, fluorenyls, indanyls and tetralinyls. The aryl radicals can also be fused to other saturated, (partially) unsaturated or aromatic ring systems. Each aryl radical can be present in unsubstituted or mono- or polysubstituted form, wherein the aryl substituents can be identical or different and can be at any desired and possible position of the aryl. Phenyl or naphthyl radicals are particularly advantageous.

The expression "heteroaryl" denotes a 5-, 6- or 7-membered cyclic aromatic radical containing at least 1, optionally also 2, 3, 4 or 5 heteroatoms, wherein the heteroatoms can be identical or different and the heterocycle can be unsubstituted or mono- or polysubstituted; if the heterocycle is substituted, the substituents can be identical or different and can be at any desired and possible position of the heteroaryl. The heterocycle can also be part of a bicyclic or polycyclic system having up to 14 ring members. Preferred heteroatoms are nitrogen, oxygen and sulfur. It is preferable for the heteroaryl radical to be selected from the group including pyrrolyl, indolyl, furyl (furanyl), benzofuranyl, thienyl(thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the binding to the compounds having the general structure I can be made via any desired and possible ring member of the heteroaryl radical.

In connection with definitions of substituents, "alkyl" denotes "$C_{1-5}$ alkyl" unless otherwise specified.

In connection with "alkyl" and "cycloalkyl", the term "substituted" within the meaning of this invention is understood to mean the substitution of one or more hydrogen radicals with F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, $C(=O)C_{1-6}$ alkyl, $C(=S)C_{1-6}$ alkyl, C(=O)aryl, C(=S)aryl, $C(=O)C_{1-6}$ alkyl-aryl, $C(=S)C_{1-6}$ alkyl-aryl, C(=O)-heteroaryl, C(=S)-heteroaryl, C(=O)-cycloalkyl, C(=S)-cycloalkyl, $CO_2H$, $CO_2$ alkyl, $CO_2$ alkyl-aryl, $C(=O)NH_2$, C(=O)NH-alkyl, C(=O)NH-aryl, C(=O)NH-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, SO-alkyl, $SO_2$-alkyl, $SO_2NH_2$, $SO_3H$, $PO(O-C_{1-6}$ alkyl$)_2$=O, =S, wherein polysubstituted radicals are understood to mean radicals which are either substituted multiple times, e.g. twice or three times, at different or the same atoms, for example three times at the same C atom, as in the case of $CF_3$ or —$CH_2CF_3$, or at different sites, as in the case of —CH(OH)—CH=CH—$CHCl_2$. The polysubstitution can take place with identical or with different substituents. A substituent can also optionally itself be substituted, so -0 alkyl also includes inter alia —O—$CH_2$—$CH_2$—O—$CH_2$—$CH_2$—OH. It is preferred within the meaning of this invention for alkyl or cycloalkyl to be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$. It is most particularly preferable for alkyl or cycloalkyl to be substituted with OH, $OCH_3$ or $OC_2H_5$.

In connection with "aryl" or "heteroaryl", "mono- or polysubstituted" within the meaning of this invention is understood to mean the single or multiple, e.g. two, three, four or five times, substitution of one or more hydrogen atoms in the ring system with F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl,O-cycloalkyl, O-aryl, O-heteroaryl, O-alkyl-aryl, O-alkyl-heteroaryl, O-cycloalkyl, O-alkyl-OH, CHO, $C(=O)C_{1-6}$ alkyl, $C(=S)C_{1-6}$ alkyl, C(=O)aryl, C(=S)aryl, C(=O)—$C_{1-6}$ alkyl-aryl, $C(=S)C_{1-6}$ alkyl-aryl, C(=O)-heteroaryl, C(=S)-heteroaryl,

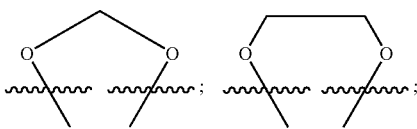

C(=O)-cycloalkyl, C(=S)-cycloalkyl, $CO_2H$, $CO_2$-alkyl, $CO_2$-alkyl-aryl, $C(=O)NH_2$, C(=O)NH-alkyl, C(=O)NH-aryl, C(=O)NH-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$; alkyl, cycloalkyl, aryl and/or heteroaryl; at one or optionally different atoms (wherein a substituent can optionally itself be substituted). The polysubstitution is performed with identical or with different substituents. It is particularly preferred within the meaning of this invention for aryl or heteroaryl to be substituted with F, Cl, Br, I, CN, $CH_3$, $C_2H_6$, $NH_2$, $NO_2$, SH, $CF_3$, OH, $OCH_3$, $OC_2H_5$ or $N(CH_3)_2$.

The term salt is understood to mean any form of the active ingredient according to the invention in which it assumes an ionic form or is charged and is coupled to a counterion (a cation or anion) or is in solution. Also included here are complexes of the active ingredient with other molecules and ions, in particular complexes which are complexed by means of ionic interactions. It means in particular (and this is also a preferred embodiment of this invention) physiologically compatible salts, in particular physiologically compatible salts with cations or bases and physiologically compatible salts with anions or acids or also a salt formed with a physiologically compatible acid or a physiologically compatible cation.

As used herein the term "physiologically compatible salt with anions or acids" is understood to mean salts of at least one of the compounds according to the invention—mostly protonated, for example on nitrogen—as cation with at least one anion, which are physiologically—particularly when used in humans and/or mammals—compatible. Within the meaning of this invention this is particularly understood to mean the salt formed with a physiologically compatible acid, namely salts of the individual active ingredient with inorganic or organic acids which are physiologically—particularly when used in humans and/or mammals—compatible. Examples of physiologically compatible salts of certain acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid and/or aspartic acid. The hydrochloride salt, the citrate and the hemicitrate are particularly preferred.

As used herein the term "salt formed with a physiologically compatible acid" is understood to mean salts of the individual active ingredient with inorganic or organic acids which are physiologically—particularly when used in humans and/or mammals—compatible. The hydrochloride and the citrate are particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharinic acid, monomethyl sebacic acid, 5-oxoproline, hexane- 1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid and/or aspartic acid.

As used herein the term "physiologically compatible salt with cations or bases" is understood to mean salts of at least one of the compounds according to the invention—mostly a (deprotonated) acid—as anion with at least one, preferably inorganic, cation, which are physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

As used herein the term "salt formed with a physiologically compatible cation" is understood to mean salts of at least one of the compounds as anion with at least one inorganic cation, which is physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

Compounds having the general formula I are preferred wherein

"alkyl substituted" or "cycloalkyl substituted" denotes alkyl or cycloalkyl substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$, and "aryl substituted" or "heteroaryl substituted" denotes aryl or heteroaryl substituted with F, Cl, Br, I, CN, $CH_3$, $C_2H_5$, $NH_2$, $NO_2$, SH, $CF_3$, OH, $OCH_3$, $OC_2H_6$ or $N(CH_3)_2$, in the form of the racemate; the enantiomers, diastereomers, mixtures of enantiomers or diastereomers or a single enantiomer or diastereomer; the bases and/or salts of physiologically compatible acids or cations.

According to one preferred embodiment of the spirocyclic cyclohexane derivatives according to the invention $R^1$ and $R^2$ together form a ring and denote —$CH_2CH_2CH_2$— or —$CH_2CH_2CH_2CH_2$—. Spirocyclic cyclohexane derivatives wherein $R^1$ and $R^2$ form a ring and together denote —$CH_2CH_2CH_2$— are particularly preferred.

Also preferred are substituted cyclohexane derivatives having the general formula I wherein $R^3$ denotes phenyl, benzyl or phenethyl, each unsubstituted or mono- or polysubstituted at the ring; $C_{1-5}$ alkyl, unsubstituted or mono- or polysubstituted; $C_{4-6}$ cycloalkyl, unsubstituted or mono- or polysubstituted; pyridyl, thienyl, thiazolyl, imidazolyl, 1,2,4-triazolyl or benzimidazolyl, unsubstituted or mono- or polysubstituted. Particularly preferred are spirocyclic cyclohexane derivatives having the general formula I, wherein $R^3$ denotes phenyl, benzyl, phenethyl, thienyl, pyridyl, thiazolyl, imidazolyl, 1,2,4-triazolyl, benzimidazolyl or benzyl, unsubstituted or mono- or polysubstituted with F, Cl, Br, CN, $CH_3$, $C_2H_5$, $NH_2$, $NO_2$, SH, $CF_3$, OH, $OCH_3$, $OC_2H_5$ or $N(CH_3)_2$; ethyl, n-propyl, 2-propyl, allyl, n-butyl, isobutyl, sec-butyl, tert-butyl, n-pentyl, isopentyl, neopentyl, n-hexyl, cyclopentyl or cyclohexyl, each unsubstituted or mono- or polysubstituted with OH, $OCH_3$ or $OC_2H_5$, wherein thienyl, pyridyl, thiazolyl, imidazolyl, 1,2,4-triazolyl and benzimidazolyl are preferably unsubstituted; in particular phenyl, unsubstituted or monosubstituted with F, Cl, CN, $CH_3$; thienyl; ethyl, n-propyl or n-butyl, unsubstituted or mono- or polysubstituted with $OCH_3$, OH or $OC_2H_5$, in particular with $OCH_3$.

In another preferred embodiment of the spirocyclic cyclohexane derivatives according to the invention $R^5$ denotes H, $CH_3$, COOH, $COOCH_3$, $CH_2O$-phenyl, wherein the phenyl radical can be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$, or $CH_2OH$. Substituted cyclohexane derivatives wherein $R^5$ denotes H are particularly preferred.

Also preferred are substituted cyclohexane derivatives having the general formula I, wherein $R^6$ can denote H; methyl, ethyl, $CF_3$, benzyl or phenyl, wherein the benzyl or phenyl radical can be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$. Spirocyclic cyclohexane derivatives wherein $R^6$ denotes H are particularly preferred.

Also preferred are spirocyclic cyclohexane derivatives wherein $R^7$, $R^8$, $R^9$ and $R^{10}$ each independently denote H; $C_{1-5}$ alkyl, branched or unbranched, unsubstituted or mono- or polysubstituted; F, Cl, Br, I, $CF_3$, OH, $OCH_3$, $NH_2$, COOH, $COOCH_3$, $NHCH_3$, thienyl, pyrimidinyl, pyridyl, $N(CH_3)_2$ or $NO_2$. Preferably one of the radicals $R^7$, $R^8$, $R^9$ and $R^{10}$ denotes H; $C_{1-5}$ alkyl, branched or unbranched, unsubstituted or mono- or polysubstituted; F, Cl, Br, I, OH, $OCH_3$, COOH, $COOCH_3$, $NH_2$, $NHCH_3$ or $N(CH_3)_2$ or $NO_2$, while the other radicals are H, or two of the radicals $R^7$, $R^8$, $R^9$ and $R^{10}$ each independently denote H; $C_{1-5}$ alkyl, branched or unbranched, unsubstituted or mono- or polysubstituted; F, Cl, Br, I, OH, $OCH_3$, COOH, $COOCH_3$, $NH_2$, $NHCH_3$ or $N(CH_3)_2$ or $NO_2$, while the other radicals are H. Spirocyclic cyclohexane derivatives wherein $R^7$, $R^8$, $R^9$ and $R^{10}$ each independently denote H, F, OH, Cl or $OCH_3$ are particularly preferred.

Compounds wherein X denotes O are particularly preferred. Compounds having the general formula I wherein X denotes $NR^{17}$ are also particularly preferred.

Most particularly preferred compounds are those from the group consisting of:

N-{6'-Fluoro-4',9'-dihydro-4-phenylspiro[cyclohexane-1,1'(3'H)-pyrano[3,4-b]indol]-4-yl}-azetidine, 2-hydroxy-1,2,3-propanetricarboxylate (2:1)

N-{6'-Fluoro-4',9'-dihydro-4-phenylspiro[cyclohexane-1,1'(3'H)-pyrano[3,4-b]indol]-4-yl}-pyrrolidine, 2-hydroxy-1,2,3-propanetricarboxylate (2:1)

N-{4',9'-Dihydro-4-phenylspiro[cyclohexane-1,1'(3'H)-pyrano[3,4-b]indol]-4-yl}-pyrrolidine, 2-hydroxy-1,2,3-propanetricarboxylate (4:3) (non-polar diastereomer)

N-{4',9'-Dihydro-4-phenylspiro[cyclohexane-1,1'(3'H)-pyrano[3,4-b]indol]-4-yl}-pyrrolidine, 2-hydroxy-1,2,3-propanetricarboxylate (1:1)

N-{6'-Fluoro-4',9'-dihydro-4-butylspiro[cyclohexane-1,1'(3'H)-pyrano[3,4-b]indol]-4-yl}-pyrrolidine, 2-hydroxy-1,2,3-propanetricarboxylate (1:1)

N-{6'-Fluoro-4',9'-dihydro-4-benzylspiro[cyclohexane-1,1'(3'H)-pyrano[3,4-b]indol]-4-yl}amine 4-(Azetidin-1-yl)-4-(3-fluorophenyl)-2',3',4',9'-tetrahydrospiro[cyclohexane-1,1'-pyrido[3,4-b]indole] (polar diastereomer)

4-(Azetidin-1-yl)-4-(3-fluorophenyl)-2',3',4',9'-tetrahydrospiro[cyclohexane-1,1'-pyrido[3,4-b]indole] (non-polar diastereomer)

4-(Azetidin-1-yl)-4-(3-fluorophenyl)-4',9'-dihydro-3'H-spiro[cyclohexane-1,1'-pyrano[3,4-b]indole] (one of two possible diastereomers)

1-(4-(Azetidin-1-yl)-4-(3-fluorophenyl)-3',4'-dihydrospiro[cyclohexane-1,1'-pyrido[3,4-b]indol]-2'(9'H)-yl)-3-phenylprop-2-en-1-one (polar diastereomer)

4-(Azetidin-1-yl)-6'-fluoro-4-(thiophen-2-yl)-4',9'-dihydro-3'H-spiro[cyclohexane-1,1'-pyrano[3,4-b]indole]2-hydroxypropane-1,2,3-tricarboxylate (1:1) (non-polar diastereomer)

optionally also as a mixture.

The substances according to the invention act for example on the ORL1 receptor which is relevant in connection with various diseases, such that they are suitable as a pharmaceutical active ingredient in a pharmaceutical composition. The invention therefore also provides pharmaceutical compositions containing at least one spirocyclic cyclohexane derivative according to the invention, optionally along with suitable additives and/or auxiliary substances and/or optionally further active ingredients.

The compounds according to the invention exhibit an affinity for the µ-opioid or for the ORL1 receptor comparable to the compounds disclosed as example compounds in WO 2004043967. In comparison to those compounds, however, they are metabolically more stable and are therefore particularly suitable for the development of pharmaceutical compositions.

The pharmaceutical compositions according to the invention optionally contain, in addition to at least one spirocyclic cyclohexane derivative according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the pharmaceutical composition is to be administered by oral, peroral, parenteral, intravenous, intraperitoneal, intradermal, intramuscular, intranasal, buccal, rectal or local means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Spirocyclic cyclohexane derivatives according to the invention in a depot formulation, in dissolved form or in a plaster, optionally with addition of agents promoting skin penetration, are suitable preparations for percutaneous administration. Preparation forms suitable for oral or percutaneous administration can deliver the spirocyclic cyclohexane derivatives according to the invention on a delayed release basis. The spirocyclic cyclohexane derivatives according to the invention can also be used in parenteral long-term depot forms, such as implants or implanted pumps, for example. Other additional active ingredients known to the person skilled in the art can be added in principle to the pharmaceutical compositions according to the invention.

The amount of active ingredient to be administered to the patient varies according to the weight of the patient, the manner of administration, the indication and the severity of the illness. 0.00005 to 50 mg/kg, preferably 0.001 to 0.5 mg/kg, of at least one spirocyclic cyclohexane derivative according to the invention are conventionally administered.

For all the above forms of the pharmaceutical composition according to the invention it is particularly preferable for the pharmaceutical composition to contain in addition to one spirocyclic cyclohexane derivative a further active ingredient, in particular an opioid, preferably a strong opioid, in particular morphine, or an anaesthetic, preferably hexobarbital or halothane.

In a preferred form of the pharmaceutical composition a spirocyclic cyclohexane derivative according to the invention is included in the form of an isolated diastereomer and/or enantiomer, which means that the stereoisomer is substantially free from the opposite stereoisomer, but not necessarily from other substances.

As was mentioned in the introduction in respect of the prior art, the ORL1 receptor has been identified in particular in the pain mechanism. Spirocyclic cyclohexane derivatives according to the invention can accordingly be used for the preparation of a pharmaceutical composition for the treatment of pain, in particular acute, neuropathic or chronic pain. The invention therefore also provides the use of a spirocyclic cyclohexane derivative according to the invention in a pharmaceutical composition for the treatment of pain, in particular acute, visceral, neuropathic or chronic pain.

The invention also provides the use of a spirocyclic cyclohexane derivative according to the invention to prepare a pharmaceutical composition for the treatment of anxiety conditions, stress and stress-related syndromes, depression, epilepsy, Alzheimer's disease, senile dementia, general cognitive dysfunctions, learning and memory disorders (as a nootropic), withdrawal symptoms, alcohol and/or drug and/or prescription drug abuse and/or dependency, sexual dysfunctions, cardiovascular diseases, hypotension, hypertension, tinnitus, pruritus, migraine, hearing impairment, gastrointestinal motility disorders, food intake disorders, anorexia, obesity, locomotive disorders, diarrhoea, cachexia, urinary incontinence, or as a muscle relaxant, anticonvulsant or anaesthetic, or for coadministration in treatment with an opioid analgesic or with an anaesthetic, for diuresis or antinatriuresis, anxiolysis, for the modulation of motor activity, for the modulation of neurotransmitter release and treatment of associated neurodegenerative diseases, for the treatment of withdrawal symptoms and/or for the reduction of the addiction potential of opioids. Optionally the spirocyclic cyclohexane derivative according to the invention may be used in the form of an isolated diastereomer and/or enantiomer, of a racemate or of a non-equimolar or equimolar mixture of diastereomers and/or enantiomers.

The invention also provides a process for the treatment, in particular in one of the aforementioned indications, of a non-human mammal or human requiring treatment of pain, in particular chronic pain, by administration of a therapeutically active dose of a spirocyclic cyclohexane derivative according to the invention or of a pharmaceutical composition according to the invention.

The invention also provides a process for the preparation of the spirocyclic cyclohexane derivatives according to the invention, as described in the following description and examples. A process for the preparation of a spirocyclic cyclohexane derivative according to the invention is particularly suitable wherein a cyclohexanone derivative having the general formula E is reacted with an indole derivative having the general formula F or H.

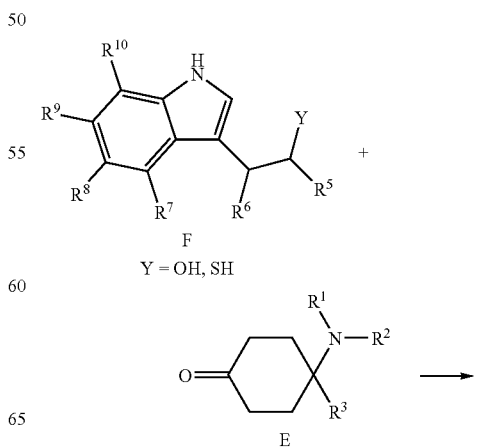

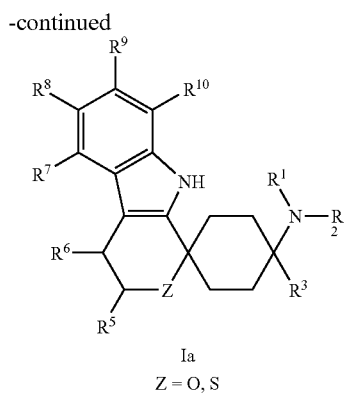

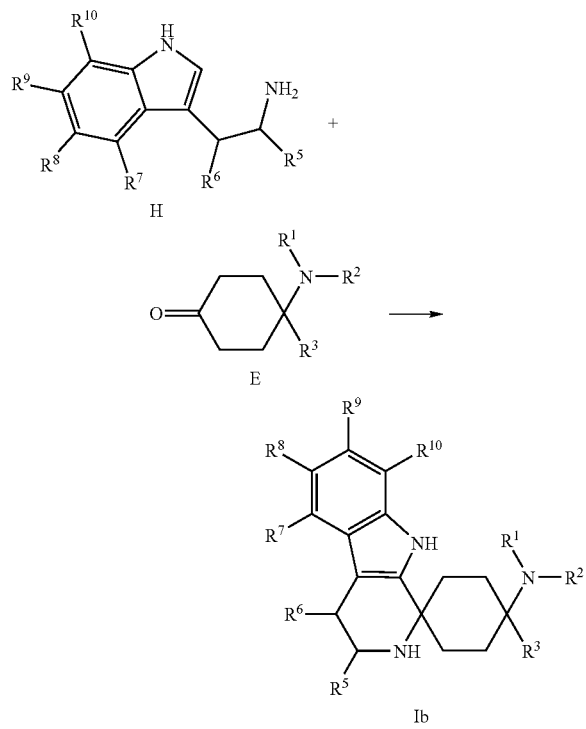

Tryptophols of type F (Y=O) can be reacted in oxa-Pictet-Spengler reactions and tryptamines of type H in Pictet-Spengler reactions, with ketones and the addition of at least one suitable reagent from the group comprising acids, acid anhydrides, esters or weakly acid-reacting salts or Lewis acids to form products having formula I. For X=SH the reaction proceeds in an analogous manner.

Preferably, at least one reagent is used from the group comprising carboxylic acids, phosphoric acids or sulfonic acids or the anhydrides thereof, carboxylic acid trialkylsilyl esters, acid-reacting salts, mineral acids or Lewis acids selected from the group consisting of boron trifluoride, indium(III) chloride, titanium tetrachloride, aluminium(III) chloride, or with the addition of at least one transition metal salt, preferably with the addition of at least one transition metal triflate (transition metal trifluoromethane sulfonate), particularly preferably with the addition of at least one transition metal trifluoromethane sulfonate selected from the group consisting of scandium(III) trifluoromethane sulfonate, ytterbium(III) trifluoromethane sulfonate and indium (III) trifluoromethane sulfonate, optionally with the addition of celite, with solid phase-bonded reactants or reagents, at elevated or reduced temperature, with or without microwave radiation, optionally in a suitable solvent or solvent blend, such as for example chlorinated or unchlorinated, preferably aromatic hydrocarbons, acetonitrile; in ethereal solvents, preferably in diethyl ether or THF; or in nitromethane, in suitable cases also in alcohols or water.

Pyridinium para-toluene sulfonate, phosphorus pentaoxide in the presence of celite, boron trifluoride etherate, trifluoroacetic acid, ortho-titanic acid tetraisopropyl ester together with trifluoroacetic acid, trifluoromethanesulfonic acid trimethylsilyl ester, trifluoromethanesulfonic acid, methanesulfonic acid, trifluoroacetic acid, acetic acid, phosphoric acid, polyphosphoric acid, polyphosphate ester, p-toluene sulfonic acid, hydrochloric acid HCl gas, sulfuric acid together with acetate buffer, tin tetrachloride, are particularly preferably used.

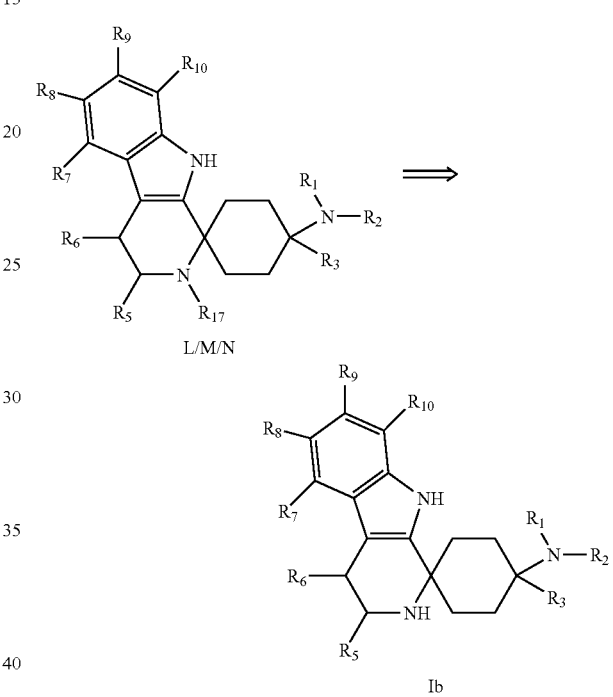

Secondary amines of type Ib can be acylated, sulfonylated or carbamoylated by methods known to the person skilled in the art to form compounds of the type L/M/N. These reactions are preferably performed at elevated temperature, particularly preferably under microwave radiation. Such methods are known to persons skilled in the art, for example, the reaction with an anhydride or an acid chloride with addition of a base, for example triethylamine.

Synthesis of Ketone Structural Units

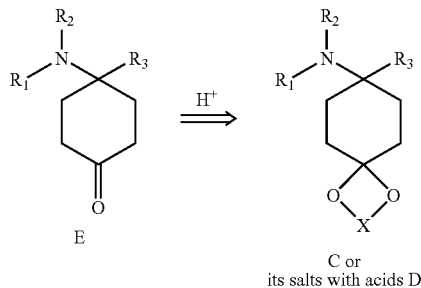

Compounds of formula E can be released from corresponding acetals C or from their salts D, by methods known to persons skilled in the art, by deprotection using acids. X here is selected from the group consisting of alkyl, alkyl/alkylidene/(saturated/unsaturated) aryl- or alkyl-substituted alkylidene.

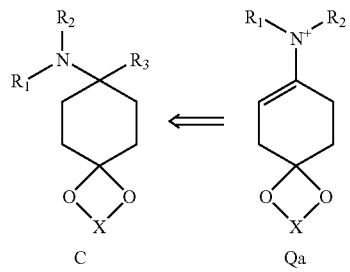

Amino acetals C having two substituents at the nitrogen atom can also be obtained by methods known to the person skilled in the art by the addition of carbon nucleophiles to salts of enamines Qa, preferably with organometallic compounds in inert solvents.

The preparation of imines is known from the literature.

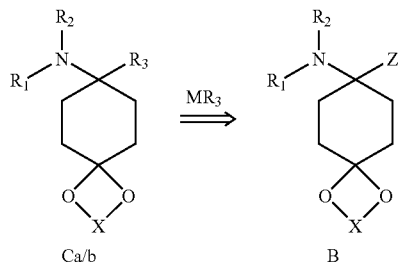

Acetals C can generally also be obtained by substitution of suitable leaving groups Z in structures having formula B. Suitable leaving groups are preferably cyano groups; 1,2,3-triazol-1-yl groups. Other suitable leaving groups are 1H-benzo[d][1,2,3]triazol-1-yl groups and pyrazol-1-yl groups (Katritzky et al., Synthesis 1989, 66-69). A particularly preferred route to compounds having structure C is the reaction of aminonitriles B with corresponding organometallic compounds, preferably Grignard compounds, preferably in ethers, preferably at room temperature. The organometallic compounds are either commercially available or can be prepared by known methods. Another particularly preferred route to compounds having structure C is the reaction of aminotriazoles B with corresponding organometallic compounds, preferably Grignard compounds, preferably in ethers, preferably at room temperature. The organometallic compounds are either commercially available or can be prepared by methods known from the literature.

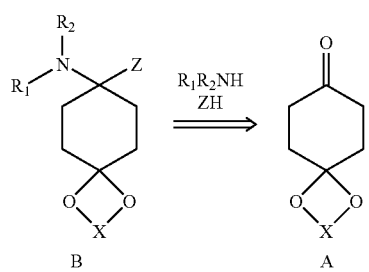

Structures having formula B can be prepared by reacting ketones A with amines and acid reactants Z—H. Suitable reactants Z—H are for example hydrogen cyanide, 1,2,3-triazole, benzotriazole or pyrazole. A particularly preferred route to compounds having structure B is the reaction of ketones with metal cyanides and the corresponding amine in the presence of acid, preferably in an alcohol, at temperatures of −40 to 60° C., preferably at room temperature, with alkali metal cyanides in methanol. A further particularly preferred route to compounds having structure B is the reaction of ketones with 1,2,3-triazole and the corresponding amine under dehydrating conditions, preferably using a water separator, at elevated temperature in an inert solvent or using molecular sieve or another desiccant. Analogue structures having benzotriazole or pyrazole groups in place of triazole groups can be introduced into B in an analogous manner.

Compounds having the general formulas F and H are either commercially available or their preparation is known from the prior art or can be derived from the prior art in a manner which is obvious to persons skilled in the art. The following citations are particularly relevant in this regard: Jirkovsky et al., J. Heterocycl. Chem., 12, 1975, 937-940; Beck et al., J. Chem. Soc. Perkin 1, 1992, 813-822; Shinada et al., Tetrahedron Lett., 39, 1996, 7099-7102; Garden et al., Tetrahedron, 58, 2002, 8399-8412; Lednicer et al., J. Med. Chem., 23, 1980, 424-430; Bandini et al. J. Org. Chem. 67, 15; 2002, 5386-5389; Davis et al., J. Med. Chem. 35, 1, 1992, 177-184; Yamagishi et al., J. Med. Chem. 35, 11, 1992, 2085-2094; Gleave et al.; Bioorg. Med. Chem. Lett. 8, 10, 1998, 1231-1236; Sandmeyer, Helv. Chim. Acta; 2; 1919; 239; Katz et al.; J. Med. Chem. 31, 6, 1988; 1244-1250; Bac et al. Tetrahedron Lett. 1988, 29, 2819; Ma et al. J. Org. Chem. 2001, 66, 4525; Kato et al. J. Fluorine Chem. 99, 1, 1999, 5-8.

EXAMPLES

The following examples are intended to describe the invention in further detail but do not limit the overall scope of the invention. The yields of the compounds produced are not optimized. All temperatures are uncorrected.

The term "ether" denotes diethyl ether, "EE" denotes ethyl acetate and "DCM" denotes dichloromethane. "Equivalent" denotes equivalent amount of substance, "mp" denotes melting point or melting range, "decomp" denotes decomposition, "RT" denotes room temperature, "abs" denotes absolute (anhydrous), "rac" denotes racemic, "conc" denotes concentrated, "min" denotes minutes, "h" denotes hours, "d" denotes days, "vol. %" denotes percent by volume, "m %" denotes percent by mass and "M" gives the concentration in mol/l.

Silica gel 60 (0.040-0.063 mm) from E. Merck, Darmstadt, was used as the stationary phase for column chromatography. The thin-layer chromatographic analyses were performed using HPTLC chromatoplates, silica gel 60 F 254, from E. Merck, Darmstadt. The mixing ratios of mobile solvents for chromatographic analyses are always given in volume/volume.

Keto Structural Unit 1

4-Azetidin-1-yl-4-phenylcyclohexanone

Stage 1: 8-Azetidin-1-yl-1,4-dioxaspiro[4,5]decane-8-carbonitrile 1,4-Dioxaspiro[4,5]decan-8-one (4.84 g, 31 mmol) followed by potassium cyanide (4.85 g, 74.4 mmol) in water (15 ml) were added with ice cooling to a mixture of 4 N hydrochloric acid (8.1 ml), methanol (4.9 ml) and azetidine (8.5 g, 10 ml, 149 mmol). The mixture was stirred at room temperature for 5 days, then water (50 ml) was added and the mixture was extracted with diethyl ether (3×50 ml). The combined organic phases were dried with sodium sulfate and concentrated to small volume under vacuum. Yield: 6.77 g (98%), oil $^1$H-NMR (DMSO-$d_6$): 1.45-1.63 (m, 4H); 1.67-1.82 (m, 4H); 1.99 (q, 2H, J=7.1 Hz); 3.21 (t, 4H, J=7.1 Hz); 3.86 (s, 4H).

Stage 2: 1-(8-Phenyl-1,4-dioxaspiro[4,5]dec-8-yl)azetidine

A solution of 8-azetidin-1-yl-1,4-dioxaspiro[4,5]decane-8-carbonitrile (2.20 g, 9.9 mmol) in anhydrous tetrahydrofuran (25 ml) was added dropwise under argon and with ice cooling to a 2 M solution of phenyl magnesium chloride in tetrahydrofuran (12 ml, 24 mmol) and then the mixture was stirred overnight at room temperature. After adding saturated ammonium chloride solution (5 ml) and water (5 ml) the phases were separated and the aqueous phase was extracted with diethyl ether (3×50 ml). The combined organic phases were dried with sodium sulfate and concentrated to small volume under vacuum. The crude product was purified by flash chromatography (100 g, 20×4.0 cm) with ethyl acetate/cyclohexane (1:1). Yield: 670 mg (25%), colorless oil.

$^1$H-NMR (DMSO-$d_6$): 1.27-1.40 (m, 2H); 1.55-2.00 (m, 8H); 2.86 (t, 4H, J=6.8 Hz); 3.76-3.89 (m, 4H); 7.24-7.45 (m, 5H).

Stage 3: 4-Azetidin-1-yl-4-phenylcyclohexanone (Keto Structural Unit 1)

6 N Hydrochloric acid (2 ml) was added to a solution of 1-(8-phenyl-1,4-dioxaspiro[4,5]dec-8-yl)azetidine (370 mg, 1.3 mmol) in acetone (30 ml) and the mixture was stirred overnight at room temperature. The pH was adjusted to 10 by the addition of 5 N sodium hydroxide solution and the aqueous phase was extracted with dichloromethane (3×20 ml). The combined organic phases were dried with sodium sulfate and concentrated to small volume under vacuum. Yield: 274 mg (92%), white solid. Melting point: not determinable $^1$H-NMR (DMSO-$d_6$): 1.67 (td, 2H, J=13.8, 6.9 Hz); 1.95-2.13 (m, 4H); 2.20-2.33 (m, 2H); 2.40-2.47 (m, 1H); 2.52-2.57 (m, 1H); 2.94 (t, 4H; J=6.9 Hz); 7.28-7.47 (m, 5H).

Keto Structural Unit 2

4-Pyrrolidin-4-yl-4-phenylcyclohexanone

Stage 1: 8-Pyrrolidin-1-yl-1,4-dioxaspiro[4,5]decane-8-carbonitrile

Pyrrolidine (22.5 ml, 0.306 mol), cyclohexane-1,4-dione monoethylene ketal (10.0 g, 0.064 mol) and potassium cyanide (10.0 g, 0.15 mol) were added with ice cooling to a mixture of 4N hydrochloric acid (17 ml) and methanol (10 ml). The mixture was stirred for 74 h at room temperature and then after adding water (80 ml) it was extracted with diethyl ether (4×70 ml). After concentration to small volume the residue was taken up in dichloromethane (70 ml) and dried overnight with magnesium sulfate. The organic phase was concentrated to small volume and the ketal 8-pyrrolidin-1-yl-1,4-dioxaspiro[4,5]decane-8-carbonitrile was obtained as a white solid with a melting point of 65-67° C. in a yield of 68% (10.2 g).

Stage 2: 4-(8-Phenyl-1,4-dioxaspiro[4,5]dec-8-yl)pyrrolidine hydrochloride

The aminonitrile 8-pyrrolidin-1-yl-1,4-dioxaspiro[4,5]decane-8-carbonitrile (10.0 g, 42.6 mmol), dissolved in THF (90 ml), was added under argon and with ice cooling within 15 min to a 1.82M phenyl magnesium chloride solution in THF (70 ml, 0.127 mol) and the mixture was stirred for 16 h at room temperature. The reaction mixture was processed by adding saturated ammonium chloride solution (100 ml) with ice cooling and was then extracted with diethyl ether (3×100 ml). The organic phase was extracted by shaking with water (70 ml) and saturated NaCl solution (70 ml) and concentrated to small volume. A yellow crystal paste (11.8 g) was retained which in addition to the desired product still contained the ketal 8-pyrrolidin-1-yl-1,4-dioxaspiro[4,5]decane-8-carbonitrile. The crude product was dissolved in ethyl methyl ketone (70 ml) and ClSiMe$_3$ (8 ml, 0.063 mol) was added with ice cooling. After a reaction time of 6 h the hydrochloride 4-(8-phenyl-1,4-dioxaspiro[4,5]dec-8-yl)pyrrolidine hydrochloride was able to be isolated as a white solid in a yield of 43% (5.9 g).

Stage 3: 4-Pyrrolidin-4-yl-4-phenylcyclohexanone (Keto Structural Unit 2)

The hydrochloride 4-(8-phenyl-1,4-dioxaspiro[4,5]dec-8-yl)pyrrolidine hydrochloride (5.8 g, 17.9 mmol) was dissolved in 7.5N hydrochloric acid (16 ml) and stirred for 24 h at room temperature. On completion of hydrolysis the reaction mixture was extracted with diethyl ether (2×50 ml), the aqueous phase was made alkaline using 5N sodium hydroxide solution with ice cooling, extracted with dichloromethane (3×50 ml) and concentrated to small volume. The ketone 4-pyrrolidin-4-yl-4-phenylcyclohexanone was able to be isolated as a yellow solid with a melting point of 75-79° C. and a yield of 96% (4.1 g).

Keto Structural Unit 3

4-Butyl-4-pyrrolidin-1-yl cyclohexanone

Stage 1: 1-(8-Pyrrolidin-1-yl-1,4-dioxaspiro[4,5]dec-8-yl)-1H-[1,2,3]triazole

Pyrrolidine (1.95 g, 2.29 ml, 27.5 mmol), 1,2,3-triazole (2.07 g, 30 mmol) and molecular sieve 4 Å (7.14 g) were added to a solution of 1,4-dioxaspiro[4,5]decan-8-one (3.9 g, 25 mmol) in toluene (40 ml). The mixture was stirred for 7 h at 90° C. Then the solution was decanted and immediately reacted further.

Stage 2: 1-(8-Butyl-1,4-dioxaspiro[4,5]dec-8-yl)pyrrolidine

The reaction solution of triazole derivatives prepared above (approx. 6.9 g, 25 mmol) in toluene (38 ml) was added dropwise to a 2 M solution of n-butyl magnesium chloride (25 ml, 50 mmol) in tetrahydrofuran under argon and with ice cooling. The reaction mixture was stirred overnight at room temperature and then poured into saturated ammonium chloride solution (60 ml). The phases were separated and the aqueous phase was extracted with diethyl ether (3×70 ml). The combined organic phases were dried with sodium sulfate, concentrated to small volume under vacuum and the residue (12 g) was purified by flash chromatography (400 g, 20×7.6 cm) with ethyl acetate/methanol (9:1). Yield: 2.70 g (40% over two stages), brown oil.

$^1$H-NMR (DMSO-$d_6$): 0.87 (t, 3H, J=7.1 Hz); 1.12-1.29 (m, 4H); 1.30-1.45 (m, 4H); 1.46-1.60 (m, 4H); 1.61-1.75 (m, 6H); 1.93 (t, 1H, J=7.1 Hz); 2.36 (t, 1H, J=7.0 Hz), 2.58 (br s, 2H), 3.83 (s, 4H).

Stage 3: 4-Butyl-4-pyrrolidin-1-yl cyclohexanone (Keto Structural Unit 3)

Water (10.0 ml) and 37% hydrochloric acid (14.0 ml) were added to a solution of 1-(8-butyl-1,4-dioxaspiro[4,5]dec-8-yl)pyrrolidine (2.70 g, 10.1 mmol) in acetone (100 ml) and the mixture was stirred overnight at room temperature. Then 4 M sodium hydroxide solution was added slowly to the mixture until a pH of 10 was achieved. The mixture was extracted with diethyl ether (4×40 ml), the combined organic phases were dried with sodium sulfate and concentrated to small volume under vacuum. The crude product (2.6 g) was purified by flash chromatography (260 g, 30×5.6 cm) with ethyl acetate/methanol (9:1). Yield: 1.06 g (47%), brown oil.

$^1$H-NMR (DMSO-$d_6$): 0.88 (t, 3H, J=6.7 Hz); 1.14-1.34 (m, 4H); 1.40-1.50 (m, 2H); 1.62-1.88 (m, 8H); 2.04 (dt, 2H, J=15.0, 3.9 Hz); 2.42 (ddd, 2H, J=6.3, 11.8, 15.5 Hz); 2.63 (t, 4H, J=6.0 Hz).

Keto Structural Unit 4

4-Benzyl-4-(4-methoxybenzylamino)cyclohexanone

Stage 1: (1,4-Dioxaspiro[4,5]dec-8-ylidene)-(4-methoxybenzyl)amine

Molecular sieve 4 Å (6 g) was added to a solution of 1,4-dioxaspiro[4,5]decan-8-one (4.69 g, 30 mmol) and 4-methoxybenzylamine (5.35 g, 5.06 ml, 39 mmol) in anhydrous tetrahydrofuran (45 ml) and the mixture was stirred for 20 h at room temperature. For analytical purposes an aliquot portion of the solution was removed and concentrated to small volume under vacuum.

$^1$H-NMR (CDCl$_3$): 1.76-1.87 (m, 2H); 1.91 (t, 2H, J=6.4 Hz); 2.53 (t, 4H, J=6.5 Hz); 3.79 (s, 3H); 4.00 (s, 4H); 4.49 (s, 2H); 6.85 (d, 2H, J=7.9 Hz); 7.21 (d, 2H, J=8.1 Hz).

The sample contains 4-methoxybenzylamine. The reaction mixture was filtered and the reaction solution used in the next stage with no further processing.

Stage 2: (8-Benzyl-1,4-dioxaspiro[4,5]dec-8-yl)(4-methoxybenzyl)amine

In a heated flask a 0.6 M solution of (1,4-dioxaspiro[4,5]dec-8-ylidene)-(4-methoxybenzyl)amine in tetrahydrofuran (17 ml, 10 mmol) was added slowly dropwise under argon and with ice cooling to a 2 M solution of benzyl magnesium chloride in tetrahydrofuran (10 ml, 20 mmol). The mixture was stirred for 20 h at room temperature and then added dropwise to 20% ammonium chloride solution (20 ml) with iced water cooling. The organic phase was separated off and the aqueous phase was extracted with diethyl ether (3×20 ml). The combined organic phases were washed with 2 N sodium hydroxide solution (20 ml) and water (20 ml), dried with sodium sulfate and concentrated to small volume under vacuum. The crude product (3.7 g) was purified by flash chromatography (370 g, 22×7.5 cm) with ethyl acetate/cyclohexane (1:2) with 1% triethylamine. Yield: 1.27 g (34%), yellowish oil.

$^1$H-NMR (CDCl$_3$): 1.53-1.66 (m, 6H); 1.89-2.03 (m, 2H); 2.77 (s, 2H); 3.76 (s, 2H); 3.80 (s, 3H); 3.95 (s, 4H); 6.82-6.88 (m, 2H); 7.12-7.37 (m, 7H). An exchangeable proton was not identified.

Stage 3: 4-Benzyl-4-(4-methoxybenzylamino)cyclohexanone (Keto Structural Unit 4)

6 M hydrochloric acid (7 ml) was added to a solution of (8-benzyl-1,4-dioxaspiro[4,5]dec-8-yl)(4-methoxybenzyl)amine (1.2 g, 3.3 mmol) in acetone (17 ml). The reaction solution was stirred for 20 h at room temperature, then made alkaline (pH~9) with 25% potassium carbonate solution and extracted with diethyl ether (3×20 ml). The combined organic phases were dried with sodium sulfate and concentrated to approx. 10 ml under vacuum. The precipitated deposit was filtered off and dried under vacuum. Yield: 790 mg (74%), white solid. Melting point: 122-124° C.

$^1$H-NMR (CDCl$_3$): 0.96 (br s, 1H); 1.76 (dt, 2H, J=13.6, 4.6 Hz); 1.84-1.97 (m, 2H); 2.10-2.24 (m, 2H); 2.65-2.80 (m, 2H); 2.86 (s, 2H); 3.81 (s, 3H); 3.87 (s, 2H); 6.85-6.91 (m, 2H); 7.12-7.36 (m, 7H).

Keto Structural Unit 5

4-(Azetidin-1-yl)-4-(3-fluorophenyl)cyclohexanone

Stage 1: (1-(8-(3-Fluorophenyl)-1,4-dioxaspiro[4,5]decan-8-yl)azetidine

A solution of 8-azetidin-1-yl-1,4-dioxaspiro[4,5]decane-8-carbonitrile (13.9 g, 62.53 mmol) in anhydrous tetrahydrofuran (70 ml) was added dropwise under argon and with ice cooling to a 1M solution of 3-fluorophenyl magnesium bromide in tetrahydrofuran (250 ml, 250 mmol) and then the mixture was stirred for 24 h at room temperature. Then saturated ammonium chloride solution (150 ml) was added with ice cooling and the mixture was stirred vigorously for 20 min. The phases were then separated and the aqueous phase was extracted with diethyl ether (3×50 ml). The combined organic phases were dried with sodium sulfate and concentrated to small volume under vacuum. The crude product was obtained in this way in a yield of 18 g (99%) as a yellow oil.

Stage 2: ((1-(8-(3-Fluorophenyl)-1,4-dioxaspiro[4,5]decan-8-yl)azetidine hydrochloride The crude product obtained above (18 g, 61.8 mmol) was dissolved in ethyl methyl ketone (100 ml), mixed with ClSiMe$_3$ (30 ml, 0.237 mol) with ice cooling and stirred in the open flask at room temperature. As no hydrochloride had been precipitated even after 24 h, the batch was concentrated to dryness (20 g brown oil, 99%) and used for ketal cleavage with no further purification.

Stage 3: 4-(Azetidin-1-yl)-4-(3-fluorophenyl)cyclohexanone (Keto Structural Unit 5)

A solution of the hydrochloride obtained above (20 g, 61 mmol) in water (50 ml) was mixed with concentrated hydrochloric acid (50 ml) and acetone (50 ml) and stirred for 48 h at room temperature. The pH was adjusted to 11 by the subsequent addition of 5N sodium hydroxide solution and then the aqueous phase was extracted with dichloromethane (3×100 ml). The combined organic phases were dried with sodium sulfate and concentrated to small volume under vacuum. The crude product (15 g) was purified by column chromatography [silica gel 60 (150 g); ethyl acetate (1000 ml)]. The desired ketone was obtained in this way in a yield of 6 g (40%).

Keto Structural Unit 6

4-(Azetidin-1-yl)-4-(thiophen-2-yl)cyclohexanone

Stage 1:1-(8-(Thiophen-2-yl)-1,4-dioxaspiro[4.5]decan-8-yl)azetidine

A catalytic amount of iodine was added to magnesium (5.1 g) in 50 ml diethyl ether. After 10 minutes a solution of 2-bromothiophene (5.7 g) in 10 ml THF was added to this reaction mixture. Once the Grignard reaction had started, 2-bromothiophene (15 ml) dissolved in 50 ml THF was added dropwise and on completion of the addition the mixture was stirred for two hours at room temperature. 8-Azetidin-1-yl-1,4-dioxaspiro[4,5]decane-8-carbonitrile (12 g) dissolved in 60 ml THF was added dropwise to this reaction mixture at 60-70° C. under a nitrogen atmosphere. Then the reaction mixture was stirred for 1 hour at room temperature and the reaction progress was monitored by thin-layer chromatography (50% EtOAc/hexane). Once the conversion was complete the reaction mixture was cooled to 0° C., quenched with saturated ammonium chloride solution (50 ml) and then extracted with ethyl acetate (2×100 ml). The combined organic phases were dried over Na$_2$SO$_4$. Following removal of the solvent under reduced pressure, the residue was purified by column chromatography (silica, 5-10% EtOAc/hexane). The desired product was obtained as a brown solid (10.2 g, 68%).

Stage 2: 4-(Azetidin-1-yl)-4-(thiophen-2-yl)cyclohexanone (keto structural unit 6)

50 ml 6N hydrochloric acid were added to a solution of 1-(8-(thiophen-2-yl)-1,4-dioxaspiro[4.5]decan-8-yl)azetidine (10 g) in 100 ml methanol at 0° C. and the reaction mixture was stirred for 1 hour at room temperature. The reaction course was monitored by thin-layer chromatography (75% EtOAc/hexane). Once the conversion was complete the methanol was removed by distillation and the residue was mixed with water (150 ml) and extracted with ethyl acetate (2×100 ml). The combined organic phases were dried over $Na_2SO_4$. Following removal of the solvent under reduced pressure the residue was taken up in cold water (150 ml) and the solution was stirred for 1 hour and then filtered. The residue that was retained was taken up in ethyl acetate and dried over $Na_2SO_4$. Following removal of the solvent under reduced pressure, the desired product (6.5 g, 78%) was obtained in the form of a brown solid.

Example A-1

N-{6'-Fluoro-4',9'-dihydro-4-phenylspiro[cyclohexane-1,1'(3'H)-pyrano[3,4-b]indol]-4-yl}-azetidine, 2-hydroxy-1,2,3-propanetricarboxylate (2:1) (One of Two Possible Diastereomers)

Trifluoromethanesulfonic acid (235 mg, 138 µl, 1.57 mmol) was added to a solution of 4-azetidin-1-yl-4-phenyl-cyclohexanone (keto structural unit 1) (270 mg, 1.18 mmol) and 5-fluorotryptophol (211 mg, 1.18 mmol) in anhydrous dichloromethane (30 ml) at 5-10° C. and the mixture was stirred overnight at room temperature. After the addition of 0.5 M sodium hydroxide solution (10 ml) the phases were separated and the aqueous phase was extracted with dichloromethane (3×10 ml). The combined organic phases were dried with sodium sulfate and concentrated to small volume under vacuum. The crude product (280 mg) was purified by flash chromatography (18 g, 20×2.0 cm) with ethyl acetate/cyclohexane (1:1) and 1% triethylamine. Yield: 119 mg (29%), white solid. Melting point: 249-257° C.

$^1$H-NMR (DMSO-$d_6$): 1.63-1.78 (m, 6H); 2.12 (d, 2H, J=12.6 Hz); 2.23-2.35 (m, 2H); 2.63 (t, 2H, J=5.4 Hz); 2.97 (t, 4H, J=6.7 Hz); 3.85 (t, 2H, J=5.3 Hz); 6.86 (dt, 1H, J=9.4, 2.6 Hz); 7.13 (dd, 1H, J=10.1, 2.5 Hz); 7.26-7.45 (m, 6H); 11.01 (s, 1H).

$^{13}$C-NMR (DMSO-$d_6$): 15.4; 22.0; 46.2; 56.1; 58.7; 71.6; 102.3 (d, J=23 Hz); 105.3 (d, J=5 Hz); 108.2 (d, J=26 Hz); 111.9 (d, J=10 Hz); 126.4; 126.6; 127.5; 132.4; 140.4; 141.9; 156.7 (d, J=230 Hz).

Citric acid (72 mg, 0.37 mmol) in isopropanol (5 ml) was added to a solution of the spiroether obtained above (119 mg, 0.3 mmol) in hot isopropanol (60 ml). The precipitated deposit A-1 was filtered off and dried. Yield: 120 mg (82%), white solid.

Melting point: 189-194° C.

$^1$H-NMR (DMSO-$d_6$): 1.68-1.83 (m, 6H); 2.13-2.35 (m, 4H); 2.59-2.76 (m, 4H); 3.11 (t, 4H, J=6.5 Hz); 3.85 (t, 2H, J=5.3 Hz); 6.87 (dt, 1H, J=9.5, 2.5 Hz); 7.14 (dd, 1H, J=9.9, 2.5 Hz); 7.30-7.37 (m, 2H); 7.38-7.48 (m, 4H), 10.95 (s, 1H).

$^{13}$C-NMR (DMSO-$d_6$): 15.4; 22.1; 26.3 (2 C); 30.3 (2 C); 43.1; 46.7 (2 C); 57.0; 58.7; 71.4; 72.2; 102.4 (d, J=24 Hz); 105.5 (d, J=5 Hz); 108.3 (d, J=26 Hz); 112.0 (d, J=11 Hz); 126.7 (d, J=10 Hz); 126.8; 127.7 (2 C); 132.4; 139.7; 141.8; 156.8 (d, J=230 Hz); 171.4; 175.3.

Example A-2

N-{6'-Fluoro-4',9'-dihydro-4-phenylspiro[cyclohexane-1,1'(3'H)-pyrano[3,4-b]indol]-4-yl}-pyrrolidine, 2-hydroxy-1,2,3-propanetricarboxylate (2:1) (One of 2 Possible Diastereomers)

Trifluoromethanesulfonic acid (399 mg, 232 µl, 2.66 mmol) was added to a solution of 4-pyrrolidin-4-yl-4-phenyl-cyclohexanone (keto structural unit 2) (486 mg, 2 mmol) and 5-fluorotryptophol (358 mg, 2 mmol) in anhydrous dichloromethane (20 ml) at 5-10° C. and the mixture was stirred overnight at room temperature. After the addition of 0.5 M sodium hydroxide solution (10 ml) the phases were separated and the aqueous phase was extracted with dichloromethane (3×10 ml). The combined organic phases were dried with sodium sulfate and concentrated to small volume under vacuum. The crude product (596 mg) was purified by flash chromatography (18 g, 20×1.5 cm) with ethyl acetate/cyclohexane (1:9→2:1) and 1% triethylamine. Two fractions were obtained.

Fraction 1: Yield: 390 mg (48%), white solid. Melting point: >260° C.

$^1$H-NMR (DMSO-$d_6$): 1.60-1.90 (m, 10H); 2.23 (t, 3H, J=13.1 Hz); 2.39 (d, 3H, J=12.9 Hz); 2.64 (t, 2H, J=5.3 Hz); 3.89 (t, 2H, J=5.3 Hz); 6.88 (dt, 1H, J=9.4, 2.5 Hz); 7.14 (dd, 1H, J=9.9, 2.5 Hz); 7.20-7.27 (m, 1H); 7.31-7.40 (m, 5H); 10.85 (s, 1H).

$^{13}$C-NMR (DMSO-$d_6$): 22.1; 23.3; 29.2; 30.5; 44.3; 56.5; 58.7; 71.7; 103.1 (d, J=23 Hz); 106.2 (d, J=4 Hz); 109.0 (J=26 Hz); 112.6 (d, J=10 Hz); 126.1; 126.3; 126.7; 126.8; 127.0; 127.3; 127.5 (d, J=10 Hz); 132.4; 140.8; 141.9; 157.5 (d, J=231 Hz).

Fraction 2: Yield: 140 mg (17%), white solid. Melting point: 188-191° C.

$^1$H-NMR (DMSO-$d_6$): 1.59 (br s, 4H); 1.76-1.88 (m, 1H); 2.08-2.20 (m, 2H); 2.34-2.48 (m, 3H); 2.52-2.60 (m, 2H); 2.66 (d, 1H, J=18.5 Hz); 2.80 (t, 3H, J=7.3 Hz); 3.47 (dd, 2H, J=13.1, 7.3 Hz); 4.58 (t, 1H, J=5.3 Hz); 6.22 (s, 1H); 6.77-6.84 (m, 1H); 6.81 (dt, 1H, J=8.8, 1.9 Hz); 7.12-7.24 (m, 3H); 7.32 (t, 2H, J=7.6 Hz); 7.48 (d, 2H, J=7.9 Hz); 10.07 (s, 1H).

$^{13}$C-NMR (DMSO-$d_6$): 22.9; 26.0; 28.6; 28.9; 33.4; 44.8; 58.2; 61.7; 102.7 (d, J=24 Hz); 107.9 (d, J=6 Hz); 108.7 (d, J=26 Hz); 111.4 (d, J=10 Hz); 125.7; 126.2; 126.8; 127.5; 129.1 (d, J=10 Hz); 129.3; 131.7; 138.0; 142.2; 156.6 (d, J=231 Hz).

Fraction 1 and fraction 2 are identical compounds.

Citric acid (138 mg, 0.71 mmol) in hot isopropanol (10 ml) was added to a solution of fraction 1 obtained above (230 mg, 0.57 mmol) in boiling isopropanol (180 ml). A thick, white deposit A-2 was precipitated within a few seconds, which was filtered off after cooling. Yield: 150 mg (45%), white solid. Melting point: 263-270° C.

$^1$H-NMR (DMSO-$d_6$): 1.65 (br s, 4H); 1.76 (d, 2H; J=12.5 Hz); 1.88 (t, 2H, J=13.6 Hz); 2.24 (t, 2H, J=12.4 Hz); 2.43 (d, 2H, J=12.9 Hz); 2.52-2.68 (m, 8H); 2.72 (d, 2H, J=15.3 Hz); 3.88 (t, 2H, J=5.4 Hz); 6.88 (dt, 1H, J=9.4, 2.6 Hz); 7.14 (dd, 1H, J=9.94, 2.47 Hz); 7.22-7.30 (m, 1H); 7.31-7.46 (m, 5H); 10.79 (s, 1H).

$^{13}$C-NMR (DMSO-$d_6$): 22.1; 29.1; 30.4; 43.0; 44.9; 57.6; 58.8; 71.6; 72.2; 102.3; 102.4 (d, J=23 Hz); 105.6 (d, J=5 Hz); 108.3 (d, J=26 Hz); 111.9 (d, J=11 Hz); 126.6; 126.8; 127.5; 132.4; 140.0; 141.7; 156.7 (d, J=231 Hz); 171.3; 175.1.

Example A-3

N-{4',9'-Dihydro-4-phenylspiro[cyclohexane-1,1'(3'H)-pyrano[3,4-b]indol]-4-yl}-pyrrolidine, 2-hydroxy-1,2,3-propanetricarboxylate (4:3) (Non-Polar Diastereomer)

Keto structural unit 2 (4-pyrrolidin-4-yl-4-phenylcyclohexanone) (243 mg, 1 mmol) was measured out together with tryptophol (161 mg, 1 mmol) in absolute dichloromethane (50 ml). Then methanesulfonic acid (0.13 ml, 2 mmol) was added. The batch was stirred for 16 hours at room temperature, during which time no precipitation was observed. 1N NaOH (20 ml) was added to the reaction mixture, and it was stirred for one hour. The organic phase was separated, and the aqueous phase was extracted with dichloromethane (2×20 ml). The organic phases were combined, dried and concentrated to small volume. The desired spiroether was obtained as a mixture of diastereoisomers (303 mg, 78%).

The spiroether diastereoisomer mixture obtained above (303 mg, 0.78 mmol) was extracted by stirring for 15 min with methanol (60 ml), the residue was separated by filtration (248 mg) and recrystallized from 2-propanol (150 ml). The non-polar spiroether (89 mg) was precipitated first. The filtrate was concentrated to small volume and once again a mixture of diastereoisomers was retained (103 mg).

The pure, non-polar spiroether (89 mg, 0.23 mmol) obtained above was mixed with ethanol (45 ml) and heated to 60° C. Citric acid in ethanol (48 mg, 0.25 mmol, 5 ml) was added to this suspension and the mixture was stirred for 10 min at 60° C. and for 1 h at room temperature. The non-polar citrate A-3 was siphoned off and isolated as a colorless solid (75 mg, 17%) with a melting point of 259° C.

Example A-4

N-{4',9'-Dihydro-4-phenylspiro[cyclohexane-1,1'(3'H)-pyrano[3,4-b]indol]-4-yl}-pyrrolidine, 2-hydroxy-1,2,3-propanetricarboxylate (1:1, Polar Diastereomer)

The spiroether diastereoisomer mixture (103 mg, 0.285 mmol) retained in example A-3 was dissolved in ethanol (80 ml) at 60° C. and citric acid in ethanol (54 mg, 0.28 mmol, 5 ml) was added at elevated temperature. The mixture was stirred for 1 h at room temperature and the non-polar citrate initially precipitated (85 mg, 19%) was separated off by filtration. The filtrate was concentrated to 2 ml, mixed with diethyl ether (40 ml) and the precipitated colourless solid was siphoned off. The polar citrate A-4 was obtained in a yield of 16% (73 mg) and with a melting point of 179-180° C.

Example A-5

N-{6'-Fluoro-4',9'-dihydro-4-butylspiro[cyclohexane-1,1'(3'H)-pyrano[3,4-b]indol]-4-yl}-pyrrolidine, 2-hydroxy-1,2,3-propanetricarboxylate (1:1) (One of 2 Possible Diastereomers)

Trifluoromethanesulfonic acid (949 mg, 552 µl, 6.3 mmol) was added to a solution of 4-butyl-4-pyrrolidin-1-yl-cyclohexanone (keto structural unit 3) (1.06 g, 4.7 mmol) and 2-(5-fluoro-1H-3-yl)ethanol (854 mg, 4.7 mmol) in anhydrous dichloromethane (60 ml) under argon and with ice cooling and the mixture was stirred for 1 day at room temperature. Then further trifluoromethanesulfonic acid (300 mg, 174 µl, 2 mmol) was added and the mixture was stirred again for 1 day at room temperature. Then the reaction mixture was mixed with 0.5 M sodium hydroxide solution (48 ml) and stirred for 20 min. The phases were separated, the aqueous phase was extracted with dichloromethane (2×20 ml) and the combined organic phases were dried with sodium sulfate. The crude product (1.8 g) was purified by flash chromatography (180 g, 20×5.6 cm) with chloroform/methanol (95:5). Yield: 370 mg (19%), yellowish solid (fraction 1). The product was in the form of the hydrochloride. The hydrogen chloride presumably comes from the chloroform used for chromatography.

$^1$H-NMR (CDCl$_3$): 0.97 (t, 3H, J=6.8 Hz), 1.35-1.41 (m, 4H); 1.46-1.52 (m, 2H); 1.57 (d, 2H, J=14.6 Hz), 1.89-1.98 (m, 4H); 2.22 (dt, 2H, J=14.6, 6.0 Hz), 2.35-2.45 (m, 2H); 2.72 (t, 2H, J=5.3 Hz), 2.78 (dt, 2H, J=14.6, 3.5 Hz); 3.10 (dt, 2H, J=13.0, 6.9 Hz), 3.63 (dt, 2H, J=12.2 and 6.6 Hz), 3.92 (t, 2H, J=5.3 Hz), 6.81 (dt, 1H, J=9.2 and 2.5 Hz), 7.06 (dd, 1H, J=9.7, 2.4 Hz), 7.37 (dd, 1H, J=8.8, 4.5 Hz); 10.36 (br s, 1H); 11.04 (s, 1H).

$^{13}$C-NMR (CDCl$_3$): 13.9; 22.6; 23.4; 25.1; 26.6; 27.0; 29.5; 32.6; 48.2; 60.3; 66.5; 71.0; 102.4 (d, J=23 Hz); 106.1 (d, J=4 Hz); 109.2 (d, J=10 Hz); 112.4 (d, J=10 Hz); 126.3 (d, J=10 Hz); 132.4; 139.8; 157.5 (d, J=233 Hz).

Contaminated product (fraction 2, 322 mg, 17%) and unreacted ketone (fraction 3, 227 mg, 23%) were also obtained.

The $^1$H-NMR spectrum of the crude product mixture shows that only one diastereoisomer and the alkene were formed, wherein the latter was not isolated.

A solution of fraction 1 (350 mg, 0.83 mmol) in chloroform (20 ml) was washed with sodium hydrogen carbonate solution, the organic phase was dried with sodium sulfate and concentrated to small volume under vacuum. Yield: 204 mg (70%), amorphous yellowish solid. Melting point: 70° C.

$^1$H-NMR (CDCl$_3$): 0.93 (t, 3H, J=6.7 Hz), 1.21-1.38 (m, 4H); 1.38-1.42 (m, 2H); 1.48 (d, 2H, J=12.8 Hz); 1.74 (d, 2H, J=12.8 Hz); 1.74-1.84 (m, 4H); 1.88 (dt, 2H, J=13.5, 2.9 Hz); 2.04 (dt, 2H, J=13.2, 3.2 Hz); 2.69 (t, 4H, J=5.8 Hz); 2.74 (t, 2H, J=5.4 Hz); 3.99 (t, 2H, J=5.4 Hz); 6.87 (dt, 1H, J=9.1, 2.5 Hz); 7.11 (dd, 1H, J=9.5, 2.4 Hz); 7.23 (dd, 1H, J=8.7, 4.3 Hz); 7.90 (s, 1H).

$^{13}$C-NMR (CDCl$_3$): 14.2; 22.5; 24.0; 24.1; 24.8; 27.0; 28.6; 30.8; 31.1; 44.1; 54.7; 59.7; 72.4; 103.2 (d, J=24 Hz); 107.1 (d, J=5 Hz); 109.4 (d, J=26 Hz); 111.2 (d, J=10 Hz); 127.6 (d, J=10 Hz); 132.0; 141.7; 157.8 (d, J=234 Hz).

A solution of the yellow solid obtained above (free base of fraction 1) (180 mg, 0.46 mmol) in hot ethanol (15 ml) was mixed with a hot solution of citric acid (90 mg, 0.46 mmol) in ethanol (1.2 ml). A white deposit was precipitated, which was filtered off after cooling. Yield: 137 mg (50%), white solid (A-5). Melting point: 198-199° C.

$^1$H-NMR (DMSO-d$_6$): 0.92 (t, 3H, J=6.7 Hz); 1.20-1.40 (m, 4H); 1.44-1.64 (m, 4H); 1.71 (br d, 2H, J=12.7 Hz); 1.90 (br s, 6H); 2.12 (br t, 2H, J=12.7 Hz); 2.57 (d, 2H, J=15.0 Hz); 2.63 (t, 2H, J=4 Hz); 2.66 (d, 2H, J=15.0 Hz); 3.07 (br s, 4H); 3.89 (t, 2H, J=5.1 Hz); 6.87 (dt, 1H, J=9.1, 2.4 Hz); 7.15 (dd, 1H, J=9.9, 2.3 Hz); 7.37 (dd, 1H, J=8.5, 4.4 Hz); 10.64 (s, 1H); approx. 11-12 (very br s, 2-3H).

Example A-6

N-{6'-Fluoro-4',9'-dihydro-4-benzylspiro[cyclohexane-1,1'(3'H)-pyrano[3,4-b]indol]-4-yl}amine Stage 1: 4-Benzyl-6'-fluoro-N-(4-methoxybenzyl)-4',9'-dihydro-3'H-spiro[cyclo-hexane-1,1'-pyrano[3,4-b]indol]-4-amine (One of 2 Possible Diastereomers)

Trifluoromethanesulfonic acid (458 mg, 266 µl, 3.05 mmol) was added dropwise with iced water cooling to a solution of 4-benzyl-4-(4-methoxybenzylamino)cyclohexanone (keto structural unit 4) (760 mg, 2.35 mmol) and 2-(5-fluoro-1H-indol-3-yl)ethanol (421 mg, 2.35 mmol) in dichloromethane (50 ml). The reaction mixture was stirred for a further 20 h at room temperature. Then the mixture was mixed with 0.5 M sodium hydroxide solution (24 ml) and then stirred for 2 h at room temperature. The organic phase was separated, and the aqueous phase was extracted with dichloromethane (3×25 ml). The combined organic phases were washed with sodium chloride solution (50 ml), dried with sodium sulfate and concentrated to small volume under vacuum. Yield: 1.07 g (94%), white solid.

Melting point: 76-79° C.

$^1$H-NMR (CDCl$_3$): 1.52 (d, 2H, J=13 Hz); 1.71-1.95 (m, 4H), 2.07 (dt, 2H, J=13.1, and 3.3 Hz); 2.74 (t, 2H, J=5.4 Hz); 2.85 (s, 2H); 3.83 (s, 3H); 3.85 (s, 2H); 3.99 (t, 2H, J=5.34 Hz); 6.81-6.97 (m, 3H); 7.06-7.41 (m, 10H), 7.96 (br s, 1H).

$^{13}$C-NMR (CDCl$_3$): 22.7; 30.7 (4); 44.9; 45.5; 53.6; 54.4; 55.5; 59.9; 72.5; 103.4 (d, J=24 Hz); 107.4; 109.7 (d, J=25 Hz); 111.5 (d, J=10 Hz); 114.2 (2); 126.5; 127.7 (d, J=10 Hz); 128.4 (2); 129.3 (2); 130.7 (2); 132.3; 133.3; 137.7; 141.5; 158.1 (d, J=233 Hz); 159.1.

A solution of citric acid (96 mg, 0.5 mmol) in ethanol (0.5 ml) was added to a hot solution of the spiroether prepared above (120 mg, 0.25 mmol) in ethanol (1 ml). After cooling, the solution was mixed with diethyl ether (20 ml). The precipitated deposit was filtered out, washed with ethanol and diethyl ether and dried under vacuum. Yield: 70 mg (41%), white solid. Melting point: 135-141° C.

$^1$H-NMR (DMSO-d$_6$): 1.53-1.84 (m, 6H); 1.95-2.15 (m, 2H); 2.62 (q, 4H, J=15.3 Hz); 2.55-2.65 (m, 2H); 2.88 (s, 2H); 3.77 (s, 3H); 3.81 (t, 2H, J=5.3 Hz); 3.97 (s, 2H); 6.86 (dt, 1H, J=9.3, 2.5 Hz); 6.98 (d, 2H, J=8.5 Hz); 7.20-7.37 (m, 7H); 7.48 (d, 2H, J=8.5 Hz); 10.66 (s, 1H).

Stage 2: 4-Benzyl-6'-fluoro-4',9'-dihydro-3'H-spiro[cyclohexane-1,1'-pyrano[3,4-b]-indol]-4-amine (A-6)

A solution of the free base of 6'-fluoro-4',9'-dihydro-N-(4-methoxybenzyl)-4-benzyl-spiro[cyclohexane-1,1'(3'H)-pyrano[3,4-b]indol]-4-amine citrate (200 mg, 0.4 mmol) in tetrahydrofuran (20 ml) and methanol (20 ml) was mixed with 10% palladium on activated carbon (40 mg) and hydrogenated for 7 h under 3 bar and at 40° C. Then the reaction mixture was filtered through a pleated filter, the filter residue was washed with methanol and the filtrate was concentrated to small volume under vacuum. The crude product (186 mg) was purified by flash chromatography (20 g, 21×2 cm) with methanol. Yield: 136 mg (64%), beige-coloured solid. Melting point 198-205° C. (decomposition).

$^1$H-NMR (DMSO-d$_6$): 1.21-1.38 (m, 2H); 1.52-1.82 (m, 5H); 1.91-2.42 (m, 3H); 2.46-2.71 (m, 4H); 3.82 (t, 2H, J=5.0 Hz); 6.78-6.89 (m, 1H); 7.04-7.31 (m, 7H); 11.0 (s, 0.7H); 11.07 (s, 0.3H).

$^{13}$C-NMR (DMSO-d$_6$): 22.0; 28.0; 28.7; 29.7; 29.9 (2); 31.6; 43.5; 50.0; 50.9; 58.7; 58.8; 71.6; 71.7; 102.4 (d, J=23 Hz); 105.4 (d, J=4 Hz); 108.3 (d, J=26 Hz); 111.7 (d, J=10 Hz); 126.5 (d, J=10 Hz); 127.7 (2); 130.6 (2C); 132.0; 132.2; 137.3; 137.9; 141.9; 156.6 (d, J=231 Hz).

Example A-7

4-(Azetidin-1-yl)-4-(3-fluorophenyl)-2',3',4',9'-tetrahydrospiro[cyclohexane-1,1'-pyrido[3,4-b]indole] (Polar Diastereomer)

Keto structural unit 5 (742 mg, 3 mmol) and tryptamine (481 mg, 3 mmol) were dissolved in MeOH (30 ml). The clear yellow reaction solution was stirred for 16 hours at room temperature. Then MeOH was removed in a rotary evaporator and the residue was dissolved in 1,2-dichloroethane (30 ml). After adding trifluoroacetic acid (3 ml, 40 mmol) the batch was stirred for 3 h at room temperature. The reaction course was monitored by DC. For processing the batch was mixed with 5N NaOH (50 ml) with ice cooling. The aqueous phase was separated off and extracted with dichloromethane (3×30 ml). The combined organic phases were dried over Na$_2$SO$_4$ and then concentrated to dryness. After adding MeOH (20 ml) a white solid was precipitated (630 mg), which was a mixture of the two diastereoisomers. The two diastereoisomers were able to be separated by column chromatography [silica gel 60 (20 g); MeOH (200 ml)]. The polar product (A-7) was obtained in a yield of 355 mg (30%) with a melting point of 186-188° C.

$^{13}$C-NMR (101 MHz; DMSO-d$_6$) δ ppm: 16.1; 22.8; 25.2; 30.4; 32.1; 34.3; 38.6; 46.0; 51.4; 59.4; 106.6; 110.8; 113.0; 113.2; 114.4; 114.6; 117.2; 117.9; 120.0; 123.7; 126.9; 129.5; 129.6; 135.4; 141.3; 141.4; 161.3; 163.7.

The non-polar product was obtained in a yield of 110 mg (9%) with a melting point of 277-281° C.

$^{13}$C-NMR (101 MHz; DMSO-d$_6$) δ ppm: 15.4; 22.8; 26.3; 30.4; 31.2; 34.3; 38.5; 46.3; 51.0; 56.5; 106.4; 111.0; 112.9; 113.1; 113.3; 113.5; 117.2; 117.9; 120.0; 122.7; 127.0; 129.0; 129.1; 135.6; 141.9; 144.1; 160.8; 163.2.

Example A-8

4-(Azetidin-1-yl)-4-(3-fluorophenyl)-2',3',4',9'-tetrahydrospiro[cyclohexane-1,1'-pyrido[3,4-b]indole] (Non-Polar Diastereomer)

Example A-8 is the non-polar diastereomer obtained in example A-7.

Example A-9

4-(Azetidin-1-yl)-4-(3-fluorophenyl)-4',9'-dihydro-3'H-spiro[cyclohexane-1,1'-pyrano[3,4-b]indole] (One of Two Possible Diastereomers)

Keto structural unit 5 (495 mg, 2 mmol) and tryptophol (322 mg; 2 mmol) were dissolved in dry dichloromethane (20 ml). Trifluoromethanesulfonic acid trimethylsilyl ester (465 µl, 2.4 mmol) was added at a temperature of 0° C. The redbrown suspension was stirred at room temperature for 16 h. The reaction course was monitored by thin-layer chromatography. For processing the batch was mixed with 5N NaOH (50 ml) with ice cooling. The aqueous phase was separated off and extracted with dichloromethane (3×30 ml). The combined organic phases were dried over Na$_2$SO$_4$ and then concentrated to dryness. The addition of MeOH (20 ml) led to the precipitation of a white solid containing one of two possible diastereoisomers. The parent liquor contained no more spiroether. A-9 was obtained in this way in a yield of 240 mg (31%) with a melting point of 270-274° C.

$^1$H NMR (400 MHz, DMSO-d$_6$) δ ppm: 1.64-1.78 (m, 6H), 2.09 (d, J=13.81 Hz, 2H), 2.22-2.40 (m, 2H), 2.66 (t, J=5.40 Hz, 2H), 2.98 (t, J=6.83 Hz, 4H), 3.87 (dd, J=12.39 Hz, 2H), 6.93-6.98 (m, 1H), 7.01-7.09 (m, 1H), 7.12-7.23 (m, 3H), 7.33-7.40 (m, 2H), 7.42-7.50 (m, 1H), 10.88 (s, 1H)

Example A-10

1-(4-(Azetidin-1-yl)-4-(3-fluorophenyl)-3',4'-dihydrospiro[cyclohexane-1,1'-pyrido-[3,4-b]indol]-2'(9'H)-yl)-3-phenylprop-2-en-1-one (Polar Diastereomer)

Cinnamic acid chloride (371 mg, 2.23 mmol) was dissolved under argon in absolute tetrahydrofuran (30 ml) and mixed at room temperature with the free base of the polar spiroamine A-7 (290 mg, 0.744 mmol), dissolved in absolute tetrahydrofuran (15 ml), within 20 min. After a reaction time of 1.5 h the cloudy reaction solution was diluted with water (10 ml), mixed with 1N sodium hydroxide solution (10 ml) with ice cooling and stirred for 2 h. Tetrahydrofuran was removed under vacuum. A solid was precipitated which was separated off by filtration and washed with water (3×5 ml). A crude product (350 mg) was isolated and separated off by chromatography [silica gel 60 (50 g); ethyl acetate (600 ml)]. The polar amide A-9 was obtained in this way in a yield of 192 mg (50%) with a melting point of 120-126° C.

$^{13}$C-NMR (101 MHz; DMSO-D$_6$) δ ppm: 22.5; 29.2; 32.6; 37.8; 41.2; 59.4; 60.4; 105.3; 111.0; 113.0; 113.2; 114.4; 114.7; 117.3; 118.3; 120.4; 123.0; 123.7; 126.5; 127.8; 128.7; 129.3; 135.1; 135.4; 139.4; 139.6; 139.7; 140.4; 161.1; 163.5; 170.2.

Example A-11

4-(Azetidin-1-yl)-6'-fluoro-4-(thiophen-2-yl)-4',9'-dihydro-3'H-spiro[cyclohexane-1,1'-pyrano[3,4-b]indole]2-hydroxypropane-1,2,3-tricarboxylate (1:1) (Non-Polar Diastereomer)

Keto structural unit 6 (706 mg, 3 mmol) was measured out together with 5-fluorotryptophol (537 mg, 3 mmol) in dichloromethane (50 ml). Then trifluoromethanesulfonic acid trimethylsilyl ester (0.64 ml, 3.3 mmol) dissolved in dichloromethane (2 ml) was added with ice cooling. The batch was stirred for 24 h at room temperature. For processing the reaction mixture was mixed with water (10 ml) and 2N NaOH (10 ml) and stirred for 20 min at room temperature. For further processing of the reaction mixture the organic phase was separated off and the remaining aqueous phase was extracted by shaking with dichloromethane (3×30 ml). The combined organic extracts were washed with water (2×20 ml) and dried over Na$_2$SO$_4$. The residue obtained after removing the solvent by distillation (1.2 g) was purified by column chromatography [silica gel 60 (50 g); ethyl acetate (500 ml)]. The non-polar diastereoisomer was obtained in a yield of 166 mg (14%) as a pale yellow oil. The polar diastereoisomer was obtained in a yield of 10 mg (<1%) as a yellow oil.

To produce the citrate the non-polar spiroether obtained above (160 mg, 0.4 mmol) was dissolved in hot isopropanol (40 ml) and mixed with a likewise hot, isopropanolic citric acid solution (80 mg, 0.4 mmol in 3 ml). The reaction mixture was then stored for 16 h in a refrigerator. The solid that was formed was siphoned off. The desired citrate was obtained in this way in a yield of 193 mg (78%) as a white solid (melting point; 174-176° C.).

$^{13}$C-NMR (101 MHz, DMSO-d$_6$) δ ppm: 14.9, 22.0, 28.5, 30.2, 38.9, 42.8, 46.5, 56.8, 58.8, 71.5, 72.3, 102.3, 102.5, 105.5, 108.2, 108.5, 111.9, 112.0, 123.8, 124.3, 126.5, 126.7, 132.4, 141.6, 145.5, 155.6, 157.9, 171.2, 174.8.

Investigations of the Effectiveness of the Compounds of the Invention:

Measurement of ORL1 Binding

The cyclohexane derivatives having the general formula I were investigated in a receptor binding assay with $^3$H-nociceptin/orphanin FQ with membranes of recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these assays was 0.5 nM. The binding assays were carried out with 20 pg amounts of membrane protein per 200 μl batch in 50 mM Hepes, pH 7.4, 10 mM MgCl$_2$ and 1 mM EDTA. The binding to the ORL1 receptor was determined using 1 mg amounts of WGA-SPA beads (Amersham-Pharmacia, Freiburg, Germany), by incubation of the batch for one hour at room temperature and subsequent measurement in a Trilux scintillation counter (Wallac, Finland). The affinity is given in Table 1 as the nanomolar K$_i$ value or in % inhibition at c=1 μM.

Measurement of μ Binding

The receptor affinity to the human μ-opiate receptor was determined in a homogeneous batch in microtitre plates. To this end, dilution series of the spirocyclic cyclohexane derivative to be tested were incubated for 90 minutes at room temperature with a receptor membrane preparation (15-40 μg protein per 250 μl incubation batch) of CHO-K1 cells, which express the human μ-opiate receptor (RB-HOM receptor membrane preparation from NEN, Zaventem, Belgium), in the presence of 1 nmol/l of the radioactive ligand [$^3$H] naloxone (NET719, NEN, Zaventem, Belgium) and 1 mg of WGA-SPA beads (wheat germ agglutinin SPA beads from Amersham/Pharmacia, Freiburg, Germany) in a total volume of 250 μl. 50 mmol/l tris-HCl supplemented with 0.05 wt. % sodium azide and 0.06 wt. % bovine serum albumin were used as the incubation buffer. In order to determine the non-specific binding, 25 μmol/l of naloxone were also added. At the end of the ninety-minute incubation period the microtitre plates were centrifuged for 20 minutes at 1000 g and the radioactivity was measured in a β counter (Microbeta-Trilux, PerkinElmer Wallac, Freiburg, Germany). The percentage displacement of the radioactive ligand from its binding to the human μ-opiate receptor was determined at a test substance concentration of 1 μmol/l and stated as the percentage inhibition (% inhibition) of the specific binding. In some cases the percentage displacement due to differing concentrations of the compounds having the general formula I to be tested was used to calculate the IC$_{50}$ inhibition concentrations which bring about a 50-percent displacement of the radioactive ligand. K$_i$ values for the test substances were obtained by extrapolation using the Cheng-Prusoff equation. In some cases determination of the Ki value was omitted and only the inhibition at a test concentration of 1 μM was determined Comparative Experiments Compounds having the same parent substance and differing only in the radicals R$^1$ and R$^2$ were compared with one another. Owing to the high affinity of the dimethyl and monomethyl compounds from WO 2004043967 for the μ-opioid receptor and for the ORL1 receptor, the affinities are given as the Ki value or as the % inhibition at a test concentration of 1 μM. This test concentration is particularly low and is suitable for the detection of compounds having a particularly high affinity.

1.) R$^3$=phenyl, R$^8$=F, R$^5$, R$^6$, R$^7$, R$^9$, R$^{10}$=H, X=O

| No. | NR$^1$R$^2$ | % inhibition (ORL1) [1 μM] | Ki (ORL1) mean [μM] | % inhibition (μ) [1 μM] | Ki (μ) mean [μM] |
|---|---|---|---|---|---|
| V-1 | ⟶N⟵ | 99 | 0.0032 | 86 | 0.0027 |

-continued

| No. | NR¹R² | % inhibition (ORL1) [1 μM] | Ki (ORL1) mean [μM] | % inhibition (μ) [1 μM] | Ki (μ) mean [μM] |
|---|---|---|---|---|---|
| V-2 | methylamino (NHCH₃) | 91 | 0.0112 | 100 | 0.0008 |
| V-3 | piperidin-1-yl | 0 | | 17 | 0.7367 |
| V-4 | morpholin-4-yl | 2 | | 8 | |
| V-5 | piperazin-1-yl | 76 | | 65 | 1.4100 |
| A-1 | azetidin-1-yl | 91 | 0.0123 | 101 | 0.0019 |
| A-2 | pyrrolidin-1-yl | 56 | 0.3833 | 98 | 0.0018 |
| V-6 | N-methyl-N-benzylamino | 18 | | 39 | |
| V-7 | phenylamino (NHPh) | −8 | 2.9000 | −16 | 6.9433 |

The two compounds V-1 and V-2 have a very high affinity for the μ-opioid and for the ORL1 receptor. In the case of the μ-opioid receptor the Ki value is in the low nanomolar range, whilst in the case of the ORL1 receptor it is in the single-digit or low double-digit nanomolar range. Replacing a $CH_3$ group with a phenyl or benzyl radical leads to compounds retaining an affinity only in the micromolar range (V-6, V-7). In the case of ring closures between the radicals $R^1$ and $R^2$ and the piperidine, morpholine or piperazine ring, the affinity is likewise not lost but drops to values in the micromolar range. Only in the case of pyrrolidine and azetidine are the nanomolar Ki values for the μ-opioid component retained. The compounds have a higher metabolic stability in comparison to the dimethyl compounds.

As shown in the table above, the N-demethyl metabolite of V-1, namely V-2, has a similarly high activity to the parent substance V-1. As an active metabolite has to undergo laborious investigations during the development of pharmaceutical compositions, the avoidance of a metabolite is advantageous. A-1 and A-2 do not form the N-demethyl metabolite. It was shown that the conversion rate of A-1 and A-2 for liver microsomes is reduced in comparison to V-1. Surprisingly, A-1 and A-2 demonstrate particularly low conversion rates for human liver microsomes as compared with mouse liver microsomes.

2.) $R^3$=phenyl, $R^5$, $R^6$, $R^7$, $R^8$, $R^9$, $R^{10}$=H, X=O

| No. | NR¹R² | % inhibition (ORL1) [1 μM] | Ki (ORL1) mean [μm] | % inhibition (μ) [1 μm] | Ki (μ) mean [μm] |
|---|---|---|---|---|---|
| V-8 | dimethylamino (N(CH₃)₂) | 98 | 0.0002 | 96 | 0.0012 |
| V-9 | morpholin-4-yl | 5 | | −3 | |

-continued

| No. | NR¹R² | % inhibition (ORL1) [1 μM] | Ki (ORL1) mean [μm] | % inhibition (μ) [1 μm] | Ki (μ) mean [μm] |
|---|---|---|---|---|---|
| A-3 | pyrrolidine (non-polar diastereomer) | 95 | 0.0035 | 94 | 0.0011 |
| A-4 | pyrrolidine (polar diastereomer) | 61 | 0.11 | 100 | 0.0098 |
| V-10 | piperidine | −2 | | 43 | |
| V-11 | piperazine | −12 | | 2 | |

Only compound A-3, in which NR¹R² denotes pyrrolidine, has an affinity for μ or for the ORL1 receptor which is comparable to V-8. The other variations of R¹ and R² lead to a worsening of the affinities.

3.) $R^3$=n-butyl, $R^8$=F, $R^5$, $R^6$, $R^7$, $R^9$, $R^{10}$=H, X=O

| No. | NR¹R² | % inhibition (ORL1) [1 μM] or Ki (ORL1) mean [μM] | % inhibition (μ) [1 μM] or Ki (μ) mean [μM] |
|---|---|---|---|
| V-12 | dimethylamine | 0.0016 μM | 0.0009 μM |
| V-13 | morpholine | 6 | 39 |

-continued

| No. | NR¹R² | % inhibition (ORL1) [1 μM] or Ki (ORL1) mean [μM] | % inhibition (μ) [1 μM] or Ki (μ) mean [μM] |
|---|---|---|---|
| A-5 | pyrrolidine | 47 | 94 |
| V-14 | piperidine | 9 | 42 |
| V-15 | piperazine | 8 | 34 |

In the series shown in 3.) too, apart from compound V-12 (NR¹R²=dimethylamine) only compound A-5 has a very high affinity for the μ-opioid receptor.

4.) $R^3$=benzyl, $R^8$=F, $R^5$, $R^6$, $R^7$, $R^9$, $R^{10}$=H, X=O

| No. | NR¹R² | % inhibition (ORL1) [1 μM] | % inhibition (μ) [1 μM] or Ki (μ) [μM] |
|---|---|---|---|
| A-6 | NH₂ | 27 | 90 |
| V-16 | piperazine (N-methyl) | 11 | 38 |
| V-17 | piperidine (N-methyl) | 5 | 39 |

| No. | NR¹R² | % inhibition (ORL1) [1 μM] | % inhibition (μ) [1 μM] or Ki (μ) [μM] |
|---|---|---|---|
| V-18 | N-methyl-N-benzyl group | 10 | 26 |
| V-19 | phenyl-NH group | 8 | -2 |
| V-20 | morpholinyl group | -3 | 7 |
| V-21 | 4-methoxybenzyl-NH group | 49 | 1.2 μM |

In the comparative series shown in 4.) $R^1$ and $R^2$=H also lead to very active compounds in comparison to a wide range of other substitution options. These compounds too have advantages in terms of metabolism. Very good affinities for the μ or ORL1 receptor were likewise determined for the following examples:

| No. | Ki (ORL1) [μM] | Ki (μ) [μM] |
|---|---|---|
| A-8 | 0.0008 | 0.0009 |
| A-9 | 0.0048 | 0.0020 |
| A-11 | 0.0066 | 0.0048 |

Comparative Analyses of Metabolic Stability

The metabolic stability of example compounds A-1 and A-2 was compared with the stability of compound V-1. For this purpose the substances were incubated in vitro with liver microsomes (mouse, human) and their metabolic stability was compared.

Methods:

Stock solutions of A-1, A-2 and V-1 of 10 mmol/l in DMSO, diluted with incubation buffer to 10 μmol/l, were used for microsome incubation. 4% BSA (bovine serum albumin) was added to the incubation buffer (100 mmol/l potassium phosphate, pH 7.4) to improve the stability of the substances in solution and to prevent non-specific losses by adsorption effects. The microsomes (mouse and human) were thawed out only shortly before the experiment and diluted with incubation buffer to 3 nmol/ml P450. The co-factor solution (10 mmol/l NADP, 10 mmol/l glucose-6-phosphate) was prepared in incubation buffer and pre-incubated for 5 min at 37° C.

The incubation batches contained 250 μl : 150 μl incubation buffer+25 μl 10 μmol/l substrate solution +25 μl microsome dilution (3 nmol P450/ml), and the enzymatic reaction was started by the addition of 50 μl co-factor solution. The incubation times were 0, 5, 10 and 15 min at 37° C. The reactions were stopped by adding 50 μl acetonitrile.

In addition to the substances to be analyzed, verapamil was also incubated as a positive control to ensure the metabolic activity of the microsomes used.

Then 50 μl of the incubation batches were made alkaline with 25 μl ammonia and extracted with 500 μl methyl tert-butyl ether. The organic phase was evaporated under nitrogen and taken up in 400 μl 50% acetonitrile/tetrahydrofuran ():1, v/v), 50% water with 0.1% formic acid.

The substances were quantified using a sensitive and specific LC-MS/MS method. Calibration samples (0.1-1 μmol/l) were prepared for the individual analytes in incubation buffer+4% bovine serum albumin and extracted with the incubation samples.

Result:

The metabolic conversion rate of A-2 with mouse microsomes is reduced by 22% as compared with V-1; with human microsomes the conversion rate is reduced to around 30% of that of V-1. For A-1 no conversion could be established with human microsomes, whereas under the same conditions the positive control verapamil was converted adequately. With mouse microsomes the rate for A-1 is reduced to less than 10% of the conversion rate for V-1.

| Substrate [1 μmol/l] | Conversion rate for human microsomes (300 pmol/ml) [nmol/min/nmol P450] | Conversion rate for mouse microsomes (300 pmol/ml) [nmol/min/nmol P450] |
|---|---|---|
| V1 | 0.0300 | 0.0255 |
| A2 | 0.0105 | 0.0200 |
| A1 | no conversion determined | 0.0009 |

Conclusion:

The rate of NADP-dependent microsomal biotransformation is reduced in the compounds according to the invention in comparison to a methylated amino group. The extent of this reduction is species-dependent and is more pronounced with human microsomes than with mouse microsomes. The ring structure itself (four-membered ring/five-membered ring) also has an influence on the conversion rate.

Parenteral Solution of a Spirocyclic Cyclohexane According to the Invention 38 g of one of the spirocyclic cyclohexane derivatives according to the invention, in this case example 3, are dissolved in 1 liter of water for injection at room temperature and then adjusted to isotonic conditions by the addition of anhydrous glucose for injection.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A spirocyclic cyclohexane compound corresponding to formula I

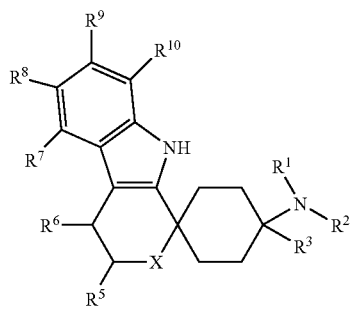

wherein $R^1$ and $R^2$ together form a ring and denote —$CH_2CH_2CH_2$— or —$CH_2CH_2CH_2CH_2$—, or $R^1$ and $R^2$ denote H;

$R^3$ denotes $C_{1-5}$ alkyl, in each case saturated or unsaturated, branched or unbranched, mono- or polysubstituted or unsubstituted; $C_{3-8}$ cycloalkyl, in each case saturated or unsaturated, mono- or polysubstituted or unsubstituted; aryl or heteroaryl, in each case unsubstituted or mono- or polysubstituted; aryl or $C_{3-8}$ cycloalkyl bonded via a $C_{1-3}$ alkyl group, in each case unsubstituted or mono- or polysubstituted;

$R^5$ denotes =O; H; $C_{1-5}$ alkyl, saturated or unsaturated, branched or unbranched, unsubstituted or mono- or polysubstituted; $COOR^{13}$, $CONR^{13}$, $OR^{13}$; $C_{3-8}$ cycloalkyl, saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted;

$R^6$ denotes H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$ alkyl, saturated or unsaturated, branched or unbranched, unsubstituted or mono- or polysubstituted; $C_{3-8}$ cycloalkyl, saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted; or $R^5$ and $R^6$ together denote $(CH_2)_n$ where n=2, 3, 4, 5 or 6, wherein individual hydrogen atoms optionally may be replaced by F, Cl, Br, I, $NO_2$, $CF_3$, $OR^{13}$, CN or $C_{1-5}$ alkyl;

at least one of $R^7$, $R^8$, $R^9$ and $R^{10}$ denotes an NHC(=O) $NR^{14}R^{15}$ group, or denotes a $SO_2NR^{14}R^{15}$ group in which at least one of $R^{14}$ and $R^{15}$ is not H, and the remainder of $R^7$, $R^8$, $R^9$ and $R^{10}$ each independently denote H, F, Cl, Br, I, $NO_2$, $CF_3$, $OR^{13}$, $SR^{13}$, $SO_2R^{13}$, $SO_2OR^{13}$, $NHC(=O)NR^{14}R^{15}$, $SO_2NR^{14}R^{15}$, CN, $COOR^{13}$, $NR^{14}R^{15}$; $C_{1-5}$ alkyl, $C_{3-8}$ cycloalkyl, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted; wherein $R^{13}$ denotes H; $C_{1-5}$ alkyl, in each case saturated or unsaturated, branched or unbranched, unsubstituted or mono- or polysubstituted; $C_{3-8}$ cycloalkyl, in each case saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted;

$R^{14}$ and $R^{15}$ each independently denote H; $C_{1-5}$ alkyl, in each case saturated or unsaturated, branched or unbranched, unsubstituted or mono- or polysubstituted; or $C_{3-8}$ cycloalkyl, in each case saturated or unsaturated, unsubstituted or mono- or polysubstituted; aryl or heteroaryl, unsubstituted or mono- or polysubstituted; or aryl, $C_{3-8}$ cycloalkyl or heteroaryl bonded via $C_{1-3}$ alkyl, unsubstituted or mono- or polysubstituted; or $R^{14}$ and $R^{15}$ together form $CH_2CH_2OCH_2CH_2$, $CH_2CH_2NR^{16}CH_2CH_2$ or $(CH_2)_{3-6}$;

$R^{16}$ denotes H; $C_{1-5}$ alkyl, saturated or unsaturated, branched or unbranched, unsubstituted or mono- or polysubstituted;

X denotes O, S, SO, $SO_2$ or $NR^{17}$;

$R^{17}$ denotes H; $C_{1-5}$ alkyl, saturated or unsaturated, branched or unbranched; $COR^{12}$ or $SO_2R^{12}$;

$R^{12}$ denotes H; $C_{1-5}$ alkyl, in each case saturated or unsaturated, branched or unbranched, mono- or polysubstituted or unsubstituted; $C_{3-8}$ cycloalkyl, in each case saturated or unsaturated, mono- or polysubstituted or unsubstituted; aryl or heteroaryl, in each case mono- or polysubstituted or unsubstituted; or aryl, $C_{3-8}$ cycloalkyl or heteroaryl bonded via $C_{1-3}$ alkyl, in each case mono- or polysubstituted or unsubstituted; $OR^{13}$, $NR^{14}R^{15}$;

or a physiologically compatible salt thereof with an acid selected from the group consisting of hydrochloric acid, hydrobromic acid, sulfuric acid, methanesulfonic acid, formic acid, acetic acid, oxalic acid, succinic acid, tartaric acid, mandelic acid, fumaric acid, lactic acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid, citric acid and aspartic acid.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein

"alkyl substituted" or "cycloalkyl substituted" denotes alkyl or cycloalkyl substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$, and "aryl substituted" or "heteroaryl substituted" denotes aryl or heteroaryl substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$.

6. A compound as claimed in claim 1, wherein $R^1$ and $R^2$ together form a ring and denote —$CH_2CH_2CH_2$— or —$CH_2CH_2CH_2CH_2$—.

7. A compound as claimed in claim 1, wherein $R^3$ denotes phenyl, benzyl or phenethyl, each unsubstituted or mono- or polysubstituted at the ring; $C_{1-5}$ alkyl, unsubstituted or mono- or polysubstituted; $C_{4-6}$ cycloalkyl, unsubstituted or mono- or polysubstituted; pyridyl, thienyl, thiazolyl, imidazolyl, 1,2,4-triazolyl or benzimidazolyl, unsubstituted or mono- or polysubstituted.

8. A compound as claimed in claim 7, wherein $R^3$ denotes phenyl, unsubstituted or monosubstituted with F, Cl, CN, $CH_3$; thienyl; ethyl, n-propyl or n-butyl, unsubstituted or mono- or polysubstituted with $OCH_3$, OH or $OC_2H_5$.

9. A compound as claimed in claim 1, wherein $R^5$ denotes H; $CH_3$; COOH; $COOCH_3$; $CH_2O$-phenyl, wherein the phenyl group optionally may be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$; or $CH_2OH$.

10. A compound as claimed in claim 1, wherein $R^6$ denotes H; methyl, ethyl, $CF_3$, benzyl or phenyl, wherein the benzyl or phenyl group optionally may be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$.

11. A compound as claimed in claim 1, wherein X denotes O.

12. A compound as claimed in claim 1, wherein X denotes $NR^{17}$.

13. A pharmaceutical composition comprising a compound as claimed in claim 1, and at least one pharmaceutically acceptable carrier or additive.

14. A composition as claimed in claim 13, wherein said compound is in the form of a salt with a physiologically compatible acid selected from the group consisting of hydrochloric acid, hydrobromic acid, sulfuric acid, methanesulfonic acid, formic acid, acetic acid, oxalic acid, succinic acid, tartaric acid, mandelic acid, fumaric acid, lactic acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid and aspartic acid.

15. A method of preparing a compound as claimed in claim 1, said method comprising reacting a compound corresponding to formula E

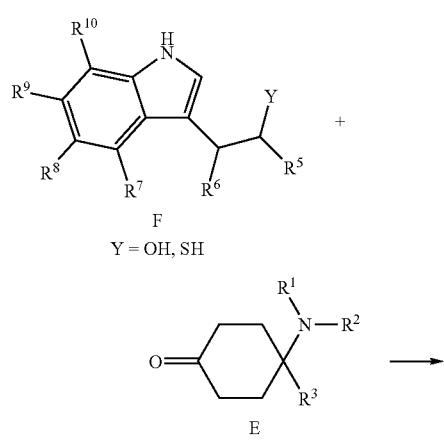

with addition of acid or a trimethylsilyl ester thereof in a suitable solvent, with a reactant corresponding to formula F or H, wherein $R^1$ to $R^3$ and $R^5$ to $R^{10}$ have the meanings given in claim 1.

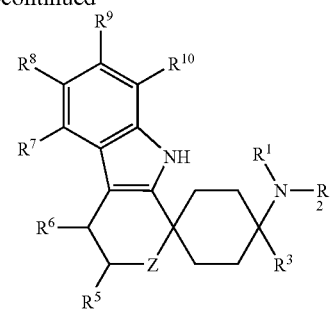

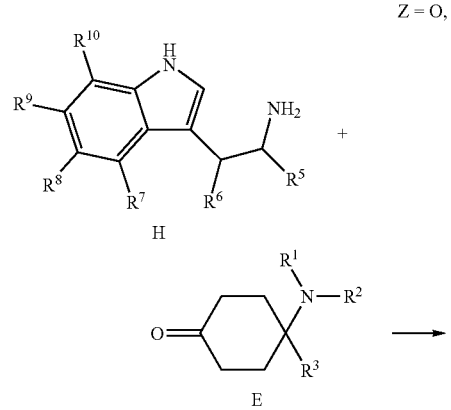

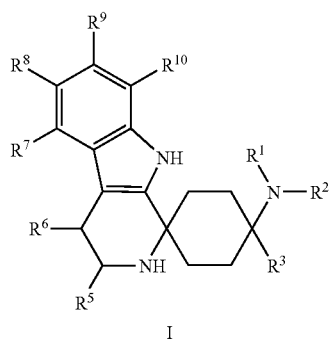

16. A method as claimed in claim 15, wherein said method is carried out in the presence of an acid selected from the group consisiting of trifluoromethanesulfonic acid trimethylsilyl ester, trifluoromethanesulfonic acid, acetic acid, phosphoric acid, methanesulfonic acid and trifluoroacetic acid, and in a solvent selected from the group consisting of dichloroethane, dichloromethane, chloroform, acetonitrile, diethyl ether and nitromethane.

17. A method as claimed in claim 15, wherein X denotes $NR^{17}$, and $R^{17}$ denotes $COR^{12}$ or $SO_2R^{12}$, said method comprising reacting a spirocyclic cyclohexane compound corresponding to formula I in which X denotes NH, with an anhydride or an acid chloride with addition of a base.

18. A method as claimed in claim 17, wherein said base is triethylamine, and the reaction is carried out under microwave radiation.

19. A method for preparing a compound as claimed in claim 1, wherein X denotes SO or $SO_2$, said method comprising oxidizing a compound corresponding to formula I wherein X denotes S with an oxidizing agent.

20. A method as claimed in claim 19, wherein said oxidizing agent is $H_2O_2$.

21. A method of treating or inhibiting pain in a subject in need thereof, said method comprising administering to said subject a pharmacologically effective amount of a compound as claimed in claim 1.

22. A method as claimed in claim 21, wherein said pain is pain selected from the group consisting of acute pain, neuropathic pain, and chronic pain.

23. A method of treating or inhibiting a condition selected from the group consisting of pain, withdrawal symptoms, alcohol or drug or prescription drug abuse or dependency, gastrointestinal motility disorders, and diarrhoea in a subject in need thereof, said method comprising administering to said subject a pharmacologically effective amount of a compound according to claim 1.

* * * * *